United States Patent [19]

Li et al.

[11] Patent Number: 5,565,616
[45] Date of Patent: Oct. 15, 1996

[54] CONTROLLED HYDROTHERMAL PROCESSING

[75] Inventors: Lixiong Li; Earnest F. Gloyna, both of Austin; Jacqueline K. McKendry, Houston, all of Tex.

[73] Assignee: Board of Regents, The University of Texas System, Austin, Tex.

[21] Appl. No.: 240,032

[22] Filed: May 9, 1994

[51] Int. Cl.$^6$ ................................. C07C 4/00
[52] U.S. Cl. ........................... 585/700; 585/733
[58] Field of Search ...................... 585/700, 733

[56] References Cited

U.S. PATENT DOCUMENTS

| | | | |
|---|---|---|---|
| 3,716,474 | 2/1973 | Hess et al. | 208/13 |
| 3,948,754 | 4/1976 | McCollum et al. | 208/11 LE |
| 3,984,311 | 10/1976 | Diesen et al. | 210/63 R |
| 4,141,829 | 2/1979 | Thiel et al. | 210/63 R |
| 4,212,735 | 7/1980 | Miller | 210/63 R |
| 4,251,227 | 2/1981 | Othmer | 48/197 R |
| 4,327,239 | 4/1982 | Dorrance | 585/733 |
| 4,473,459 | 9/1984 | Bose et al. | 208/8 LE |
| 4,543,190 | 9/1985 | Modell | 210/721 |
| 4,559,127 | 12/1985 | Paspek, Jr. | 208/8 LE |
| 4,594,141 | 6/1986 | Paspek, Jr. et al. | 208/390 |
| 4,792,408 | 12/1988 | Titmas | 210/747 |
| 4,818,370 | 4/1989 | Gregoli et al. | 208/106 |
| 4,840,725 | 6/1989 | Paspek | 208/130 |
| 4,861,497 | 8/1989 | Welch et al. | 210/759 |
| 4,898,107 | 2/1990 | Dickinson | 110/346 |
| 5,057,220 | 10/1991 | Harada et al. | 210/605 |
| 5,100,560 | 3/1992 | Huang | 210/721 |
| 5,133,877 | 7/1992 | Rofer et al. | 210/761 |
| 5,200,093 | 4/1993 | Barner et al. | 210/761 |
| 5,232,604 | 8/1993 | Swallow et al. | |
| 5,250,193 | 10/1993 | Sawicki et al. | 210/761 |

FOREIGN PATENT DOCUMENTS

| | | |
|---|---|---|
| 85597/82 | 1/1983 | Australia . |
| 8204075 | 5/1983 | Brazil . |
| 568882 | 11/1993 | European Pat. Off. . |
| 53-91093 | 8/1978 | Japan . |
| 5031000 | 9/1991 | Japan . |
| WO93/22490 | 11/1993 | WIPO . |

OTHER PUBLICATIONS

"ECO Waste Technologies and the Huntsman Corporation Host an Introduction to SCWO Technology and a Tour of Their SWCO Facilities," *Separations Update*, p. 3, Center for Energy Studies, University of Texas at Austin, Tischler, C., ed., Summer 1994.

Ladendorf, K., "Company hopes treatment cuts waste," *Austin American–Statesman*, pp. D1–D3, Aug. 25, 1994.

LeBlanc et al., "Production of Methanol," *Methanol Production and Use*, pp. 73–113, Ch. 3.3, Chen et al., eds., Marcel Dekker, Inc., New York, 1994. month not available.

Zoeller, J. R., "Manufacature via Methanol Carbonylation," *Acetic Acid and its Derivatives*, pp. 35–51, Agreda et al., eds., Marcel Dekker, Inc., New York, 1993. month not avaiable.

Gustafson and Zoeller, "Other Synthesis Gas–Based Acetic Acid Processes," *Acetic Acid and its Derivatives*, Ch. 5, pp. 53–60, Agreda and Zoeller, eds., Marcel Webber, Inc., 1993. month not avaiable.

Herman, R. G., ed., *Catalytic Conversation of Synthesis Gas and Alcohols to Chemicals*, pp. 37–283, Plenum Press, New York, 1984. month not avaiable.

(List continued on next page.)

*Primary Examiner*—Shrive Beck
*Assistant Examiner*—Timothy H. Meeks
*Attorney, Agent, or Firm*—Arnold, White & Durkee

[57] ABSTRACT

Production of alkanes from an alkyl bound to a heteroatom under controlled hydrothermal conditions at supercritical or near critical water conditions including the use of an additive. The method reduces the extent of oxidation, generates useful and recoverable products, alters product distributions, promotes product yield, and enhances reaction rates. Additives alter product distributions and neutralize or consume mineral acids.

24 Claims, 13 Drawing Sheets

OTHER PUBLICATIONS

Baker et al., "Catalytic Destruction of Hazardous Organics in Aqueous Wastes: Continuous Reactor System Experiments," *Hazardous Waste & Hazardous Materials*, 6(1):87–94, 1989. (month unknown).

Crain et al., "Kinetics and Reaction Pathways of Pyridine Oxidation in Supercritical Water," *Ind. Eng. Chem. Res.*, 32(10):2259–2268, 1993. (month unknown).

Gloyna and Li, "Testing Support of Supercritical Fluid Processing For the Destruction of Toxic Chemicals," *Interim Report*, Center for Energy Studies, Balcones Research Center, The University of Texas at Austin, Austin, TX, Nov. 30, 1993.

Holgate et al., "Carbon Monoxide Oxidation in Supercritical Water: The Effects of Heat Transfer and the Water–Gas Shift Reaction on Observed Kinetics," *Energy & Fuels*, 6:586–597, 1992. (month unknown).

Hudson and Keay, "The Hydrolysis of Phosphonate Esters," *Journal of the Chemical Society*, 2463–2469, 1956. (month unknown).

Huppert et al., "Hydrolysis in Supercritical Water: Identification and Implications of a Polar Transition State," *Ind. Eng. Chem. Res.*, 28:161–165, 1989. (month unknown).

Klein et al., "Hydrolysis in Supercritical Water: Solvent Effects as a Probe of the Reaction Mechanism," *J Supercritical Fluids*, 3:222–227, 1990. (month unknown).

McBrayer et al., "Research and Development of a Commerical Supercritical Water Oxidation Process," *Proceedings of the Eleventh Annual Environmental Management and Technology Conference/International*, Atlantic City, NJ, Jun. 9–11, 1993.

McKendry et al., "The Effective of Additives on the Oxidation of Dimethyl Methylphosphonate in Supercritical Water," *Abstract*, Industrial Waste Conference, Purdue University, West Lafayette, Indiana, May 9–11, 1994.

Tester et al., "Supercritical Water Oxidation Technology: A Review of Process Development and Fundamental Research" *ACS Symposium Series Paper.*, Oct. 1–3, Atlanta, Georgia, 1993.

Townsend et al., "Solvent Effects during Reactions in Supercritical Water", *Ind. Eng. Chem. Res.*, 27:143–149, 1988. (month unknown).

Baillod et al., "Fate of Specific Pollutants During Wet Oxidation and Ozonation," *Environ. Prog.*, 1(3), 217–227, 1982. (month unknown).

Day et al., "Oxidation of Propionic Acid Solutions," *Can. J. Chem. Eng.* 51, 733–740, 1973. (month unknown).

Conditt and Sievers, "Microanalysis of Reaction Products in Sealed Tube Wet Air Oxidations by Capillary Gas Chromatography," *Anal. Chem.*, 56:2620–2622, 1984. (month unknown).

Corcoran, "Pyrolysis of n–Butane," *Pyrolysis: Theory and Industrial Practice*, 47–69, 1983. (month unknown).

United States Environmental Protection Agency, "Gas-Phase Chemical Reduction," *Demonstration Bullentin*, EPA/540/MR–93/522, 1993. (month unknown).

Fisher, "Oxidation of Sewage With Air at Elevated Temperatures," *Water Research*, 5:187–201, 1971. (month unknown).

Hurwitz et al., "Wet Air Oxidation of Sewage Sludge," *Water & Sewage Works*, 112(8):298–305, 1965. (month unknown).

Irick, "Manufacture via Hydrocarbon Oxidation," In Acetic Acid and its Derivatives, Ed. by Agreda and Zoeller, Marcel Dekker, Inc., New York, 1993. (month unknown).

Keen and Baillod, "Toxicity to *Daphnia* of the End Products of Wet Oxidation of Phenol and Substituted Phenols," *Water Res.*, 19(6):767–772, 1985. (month unknown).

McConnell and Head, "Pyrolysis of Ethane and Propane," *Pyrolysis: Theory and Industrial Practice*, Ch. 2, 25–47, 1983. (month unknown).

McGinnis et al., "Conversion of Biomass into Chemicals with High–Temperature Wet Oxidation," *Ind. Eng. Chem. Prod. Res.*, 22(4):633–636. (date unknown).

Partin and Heise, "Bioderived Acetic Acid," Ch. 1, 3–15, 1993. (month unknown).

Taylor and Weygandt, "A Kinetic Study of High Pressure Aqueous Oxidations of Organic Compunds Using Elemental Oxygen," *Can. J. Chem.*, 52:1925–1933, 1974. (month unknown).

Teletzke et al., " Components of Sludge and Its Wet Air Oxidation Products," *Journal WPCF*, 39(6):994–1005, 1967. (month unknown).

Turner, "Supercritical Water Oxidation of Dimethyl Methylphosphonate and Thiodiglycol," *Ph.D. Dissertation*, Civil Engineering Department, The University of Texas at Austin, Austin, Texas, 1993. (month unknown).

Webley et al., "Oxidation Kinetics of Ammonia and Ammonia–Methanol Mixtures in Supercritical Water in the Temperature Range 530°–700° C. at 246 bar," *Ind. Eng. Chem. Res.*, 30:1745–1754, 1991. (month unknown).

CONTROLLED HYDROTHERMAL PROCESSING

Research leading to the present invention was supported in parts by the Advanced Research Projects Agency Contract No. LSC-EE209701. The U.S. government therefore has certain rights in the invention.

FIELD OF THE INVENTION

This invention generally relates to a conversion process in which waste materials are transformed into useful products in the presence of water and additives under supercritical and near critical conditions for water. These products may be used as a source of fuel or raw materials.

BACKGROUND OF THE INVENTION

Supercritical water oxidation (SCWO) has been demonstrated to be effective in the destruction of hazardous and toxic wastes. This chemical oxidation process takes place at temperatures above 374.15° C. and 22.1 MPa. High destruction efficiencies (>99.99%) over relatively short residence times (on the order of seconds to minutes) are achieved due to the high solubility of organic compounds and oxygen, alleviating mass transfer hindrances. Residual organic compounds, such as acetic acid, are relatively harmless and may be treated readily by conventional treatment techniques.

SCWO is currently being investigated to address the disposal of chemical warfare agents and munitions which are stored at several sites within and outside the U.S. The stockpile of chemical agents and munitions consists of several nerve and blistering agents as well as explosives or energetic materials. Dimethyl methylphosphonate, DMMP ($C_4H_{10}FO_2P$), is a simulant selected by the Department of the Army to study the behavior of the nerve agent GB, or Sarin ($C_4H_{10}FO_2P$). These two compounds are similar in structure and properties; DMMP may be used to study the potential fate of GB during SCWO, without producing harmful by-products, in particular, hydrogen fluoride gas. The present invention resulted from the study of DMMP under SCWO conditions.

FIG. 1 summarizes the reaction pathways for hydrolysis and oxidation of DMMP and its by-products. DMMP is base-hydrolyzed to form MPA and methanol at ambient conditions (Hudson et al., 1956). This pathway was confirmed in a kinetic study of hydrolysis/pyrolysis runs of DMMP in SCWO (Turner, 1993). As shown in equation A of FIG. 1, methanol and MPA were observed to form in a 2:1 ratio.

MPA may undergo hydrolysis or oxidation in supercritical water. The structure of MPA appears to meet criteria set in previous studies for compounds which are readily hydrolyzed in supercritical water (Klein et al., 1990; Townsend et al., 1988). Since the C atom is saturated and bonded to the heteroatom phosphorus, attack appears to occur at the P—C bond, producing phosphoric acid and methane as shown in equation B of FIG. 1. At least one previous study did not show this reaction pathway to be significant in kinetic studies of the supercritical water oxidation of DMMP (Turner, 1993). Significant quantities of methane do not appear to have been detected in hydrolysis and oxidation tests performed at supercritical temperatures.

Free radical oxidation of MPA was studied at ambient conditions by Mill and Gould (1979). Oxidation of MPA appears to have been found to produce carbon dioxide, water, phosphates and trace amounts of CO. Kinetic studies conducted by Turner (1993) also stated carbon dioxide, water, phosphates, carbon monoxide as well as methanol as by-products of MPA oxidation in supercritical water as shown in equation C of FIG. 1.

Oxidation of methanol may result in the intermediate production of carbon monoxide and water and further reactions producing carbon dioxide and hydrogen may occur (Webley and Tester, 1989). The concentration (% by volume) of off-gas appears to have been less than 0.01. However, significant hydrolysis of methanol does not appear to have been observed in kinetic studies by Turner (1993). The oxidation of methanol is shown in equations E, F and G in FIG. 1. Carbon monoxide oxidation in supercritical water is shown in equation G (Holgate et al., 1992). A parallel water-gas shift reaction, not shown in FIG. 1, was observed to occur. The water-gas shift reaction occurs in the absence of oxygen (typical in reactor heat-up conditions) whereby CO reacts with water to form $CO_2$ and $H_2$. Researchers found that 1.4–23% of CO conversion was due to the water-gas shift reaction. Methane oxidation in supercritical water has been studied by Webley and Tester (1991). As indicated in equation D of FIG. 1, carbon dioxide was a major by-product found, although trace amounts of carbon monoxide and hydrogen were detected. Hydrogen generation was attributable to water-gas shift reactions.

The properties of supercritical water have been demonstrated to change in the presence of additives. By altering the reaction medium, reaction mechanisms may be modified. For example, typical reactions which take place in supercritical water are homolyric in nature, whereby free radicals are formed. This is due to several properties of supercritical water, in particular, its low dielectric constant, dissociation constant and low density. Homolyric reaction mechanisms are not very selective, accounting for the high reactivity of free radicals. Heterolytic reaction mechanisms, on the other hand, are ionic in nature and are readily acid- or base-catalyzed. Hydrolysis reactions are typically heterolytic mechanisms. Because of their ionic nature and the non-polar environment of supercritical water, heterolytic reactions are not readily supported in supercritical water. However, by altering the properties of supercritical water, hydrolysis reactions may be enhanced. Heterolytic chemistry has been shown to prevail when $K_w \geq 10^{-14}$ while homolyric chemistry (free radical) prevails when $K_w \ll 10^{-14}$ (Antal et al., 1987).

At densities above 0.3 g/mL to 0.4 g/mL and at temperatures lower than 500° C., supercritical fluid retains its ionic properties (Antal et al., 1987; Xu et al., 1990). Hydrolysis and oxidation of acetamide in supercritical water was studied by Lee and Gloyna, (1990) at densities between 0.090 and 0.135 g/mL. The dielectric constant was varied between 1.5 and 5.5 and $K_w$ was varied between $10^{-16.5}$ and $10^{-24.5}$. Researchers indicated no effect of $\epsilon$ or $K_w$ on the hydrolysis of acetamide. Therefore, it was concluded, there is little dependence of hydroxyl or hydronium ions on the reaction since the concentration of these ions was so small. Since it was believed that ionic mechanisms responsible for the observations could not be supported in the low density environment due to the lack of an ionized species required for nucleophilic attack, it was proposed that the water molecule serves as the nucleophile in acetamide hydrolysis. Others proposed this mechanism for the hydrolysis of dibenzyl ether (DBE) and phenethyl phenyl ether (PPE) (Klein et al., 1990).

Pyrolysis and hydrolysis of dibenzyl ether (DBE) and benzyl phenyl amine (BPA) in supercritical water appeared to indicate an increase in the selectivity of the hydrolysis by-products upon the addition of sodium chloride (Torry et al., 1991). The selectivity was observed up to a certain concentration of salt when the presence of a second phase inhibited hydrolysis. Further, increased water density was found to increase the dielectric constant in supercritical water and stabilize the polar hydrolysis transition state over less-polar reactants (Townsend and Klein, 1985). Hydrolysis studies of guaiacol in supercritical water showed the ability of supercritical water to support heterolytic chemistry in addition to free radical mechanisms (Huppert et al., 1989).

Japanese Patent JP 5031000 relates to a method comprising selectively hydrolysing and/or pyrolysing natural or synthetic high molecular compounds using water under supercritical or subcritical conditions as solvent. British Patent BR 8204075 relates to the production of synthesis gas carried out by reacting a hydrocarbon with steam and optional $O_2$ in a steam reformer or partial oxidation gasifier. The reported improvement relates to reducing and controlling the $H_2$/CO ratio in the synthesis gas.

German Patent DE 4215087 relates to the recovery of caprolactam monomer from polycaprolactam by high pressure hydrolysis of the polymer with 5–30 wt. % water at 200°–350° C. followed by recovery of monomer from the resulting aqueous solution or suspension, including hydrolysis reportedly effected in the presence of an alkali hydroxide at pH 5–10. WO 9322490 relates to the recovery of inorganic processing chemicals, in the form of bicarbonates and/or carbonates from waste liquid in the production of cellulose by the organo-solvent process involving partial or complete oxidation of organic components in the aqueous phase with air and/or oxygen.

U.S. Pat. No. 5,133,877 relates to conversion of hazardous materials using supercritical water oxidation. U.S. Pat. No. 4,483,761 relates to the addition of light olefins in the cracking of hydrocarbons. U.S. Pat. No. 3,984,311 relates to the use of a mixture of nitrate and iodide or bromide ions in wet oxidation. U.S. Pat. No. 4,212,735 relates to the addition of a transition metal ion to the nitrate/iodide (bromide) system. U.S. Pat. No. 5,232,604 refers to the nitrate/iodide (bromide) system as undergoing oxidation/reduction reactions and are therefore reactants. This patent also refers to the reported addition of a caustic material such as NaOH to a reactor for neutralizing acids and producing salts which precipitate in the reactor. Methane was reportedly produced in catalyzed hydrothermal treatment of p-cresol and methyl isobutyl ketone (Baker et al., 1989).

Wet oxidation processes (both supercritical and subcritical water oxidation) convert complex organic compounds into simpler structured compounds. Typically, at supercritical condition, the complete conversion results in carbon dioxide, water, and mineral acids. An ideal wet oxidation process operating at near self-sustaining conditions typically requires an organic load of 5 wt % (about 50 g/L chemical oxygen demand). However, wet oxidation of relatively concentrated organic wastes imposes three basic concerns: (1) excessive corrosion by the mineral acids produced from the process; (2) long reactor residence times to achieve high organic conversions; and (3) increased consumption of high-pressure oxygen.

A goal of the present invention is control of the wet oxidation process so that incompletely oxidized intermediate compounds are optimally produced and recovered.

SUMMARY OF THE INVENTION

The present invention addresses these and other concerns regarding complete conversion of feedstock materials in SCWO. A controlled hydrothermal process demonstrated by the present invention reduces the extent of oxidation, generates useful and recoverable products, alters product distributions, promotes product yield, and enhances reaction rates. This process permits the conversion of waste materials into useful products. At the same time, this process, as compared to conventional subcritical and supercritical water oxidation processes, requires much less oxidant and imposes a lesser corrosive impact on processing equipment. The additives alter product distributions and neutralize or consume mineral acids.

The present invention provides for a method of producing an alkane comprising the steps of obtaining a reactant comprising an alkyl bound to a heteroatom, mixing with the reactant an additive reacting with the heteroatom or an oxidized heteroatom form to produce a salt insoluble in supercritical water and allowing the mixture to react in supercritical or near critical water and at an oxygen concentration favoring alkane production wherein formation of insoluble salt effects an equilibrium shift favoring alkane production.

The term "heteroatom" as used herein generally means any atom other than carbon, hydrogen or oxygen. A heteroatom or an oxidized heteroatom form, for example, forms polar salts with cations, the salts being characteristically insoluble in supercritical water. Preferred heteroatoms include phosphorus, sulfur, nitrogen, arsenic, selenium and halogens. A halogen may be the halogen of chlorocarbons or chlorofluorocarbons, for example. Most preferred heteroatoms are phosphorus, sulfur or nitrogen. For these embodiments, the oxidized heteroatom form is phosphate, sulfate or nitrate. Near critical conditions for water means those temperatures and pressures at which solubilities defined for supercritical conditions are substantially the same. Temperature ranges may be from about 350° C. to about 500° C.

The term "additive" refers to a substance added to a reaction medium that reacts with a heteroatom or an oxidized heteroatom form to produce a salt that is insoluble under supercritical conditions and therefore, precipitates. A most effective additive is preferably but not necessarily soluble in the feed. The product may absorb onto a solid surface. An additive may be an ionic species, a metal hydroxide, carbonate, borate or oxide. The metal may be an alkali, an alkaline earth or a transition metal. More preferred additives are NaOH, KOH, LiOH, $Na_2CO_3$ or $Na_2B_4O_7$. A most preferred additive is NaOH. The desired products may be the precipitate or may be a product remaining in the supercritical water phase or in the gas phase.

The reactant may be a component of wastewater, sludge, organic material, halocarbon material, or the reactant may comprise dialkyl alkylphosphonate or alkylphosphonic acid. One skilled in this art in light of the present disclosure would readily understand that various alkyl groups may be bound to a heteroatom in a reactant; such as, ethyl, propyl, butyl, pentyl, isomers thereof, or alkyl groups having up to about 20 carbon atoms, for example. Alkyl groups having up to about 6 carbon atoms are preferred. Hydrocarbon groups equivalent to alkyl would be those that behave similarly, such as, benzyl or alkenyl, for example.

An oxygen concentration optimizing alkane production may be an oxygen concentration less than about 20% stoichiometric oxygen, or may be less than about 1% stoichiometric oxygen. The alkane produced by the above method may be methane, ethane, propane, butane, isomers of butane or higher carbon alkanes. In particular, the alkane is methane.

A further embodiment of the present invention is a method of converting nitrogen of a nitrogen-containing reactant to ammonia. The method comprises the steps of mixing an oxidant with the nitrogen-containing reactant and allowing the mixture to react under supercritical or near critical water conditions at a temperature of between about 475° C. and 525° C. and for a residence time that maximizes production of ammonia.

Preferably, the temperature is about 500° C. and the residence time is from about 6 to 9 seconds. The oxidant may be oxygen and may be present in substoichiometric or stoichiometric amounts. The reactant may be wastewater, sludge or organic material having nitrogen in a reduced state, such as amines or aromatic nitrogen. Amines may be primary, secondary or tertiary.

A further embodiment of the present invention is the aforedescribed method of converting nitrogen of a nitrogen-containing reactant to ammonia comprising the further step of obtaining the ammonia by including an additive in the mixture that forms an ammonium salt. The additive may be an acid and, in particular, may be HCl.

Many industrial wastewaters contain fairly concentrated organic materials. Since one mole of organic carbon approximately reacts with one mole of oxygen and produces one mole of carbon dioxide, complete conversion of these organics requires a large amount of oxygen and produces an equivalent amount of carbon dioxide. Controlled hydrothermal reactions provided by the present invention are particularly useful and consequently more economical for processing wastewaters containing relatively high concentration of organic compounds. Such utility occurs due to the increased concentrations of recoverable by-products. The controlled hydrothermal reactions of the present invention may also be used for purposeful chemical production of products and the feed may be a chemical feedstock.

DESCRIPTION OF THE PREFERRED EMBODIMENTS

Figure 1:
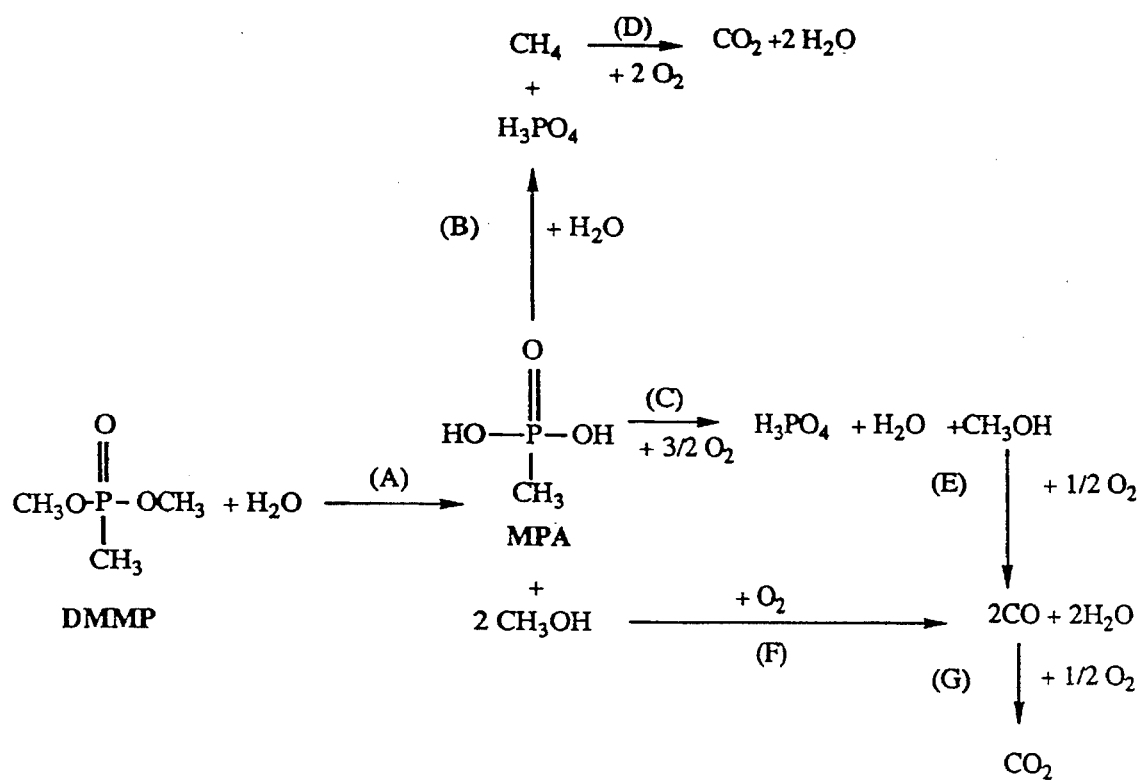
FIG. 1 shows reaction pathways for hydrolysis and oxidation of DMMP and its by-products.

The present invention provides for controlled hydrothermal processing to produce by-products as opposed to final products produced by forcing the complete oxidation of starting material. For example, in a limited oxygen environment, methane, a useful, high-energy content fuel, was produced. This production was enhanced using additives.

The effect of additives on the destruction of dimethyl methylphosphonate (DMMP, a model for organic wastes or byproducts containing a heteroatom) at supercritical conditions is presented in Example 2 while a control study without additives is presented in Example 1. The additives chosen were selected to observe their effect on by-product formation upon the destruction of DMMP in supercritical water. Additives that could behave as buffers were selected as possibly having the ability to neutralize acidic effluents generated during the SCWO process. By neutralizing the acidic effluent resulting from certain waste streams, corrosion is inhibited, and reactor lifetimes prolonged. Fixed conditions included: initial concentration of DMMP, (10,000 mg/L); residence time, (five minutes); temperature, (450° C.); and pressure, (27.6 MPa). Variables conditions included: the use of three additives (NaOH, $Na_2B_4O_7$, $Na_2CO_3$), and three oxygen concentrations (in excess of 100%, 17% and 0% of stoichiometric demand). Oxidation and hydrolysis by-products were identified and quantified as a function of oxygen concentration. By-products included methyl phosphonic acid, phosphates, and methanol in the liquid phase, and methane, carbon dioxide, carbon monoxide and hydrogen in the gas phase. The final pH was measured and corrosion products, chromium and iron, were quantified.

When greater than the stoichiometric oxygen demand for oxygen was supplied in the reaction medium, additives had little effect on the overall conversion of DMMP. Carbon dioxide generation was just as great in runs conducted with additives as with runs conducted without additives.

Under hydrolysis and partial oxidation conditions, additives supported the hydrolysis of MPA as evidenced by the production of methane. The creation of a more polar reaction medium and the relative solubilities of the intermediate MPA and the end-product phosphoric acid are two possible reasons explaining the increase in hydrolysis end-products.

In the presence of an additive, the effluent pH measured after a five minute reactor residence time was moderately increased by at least 0.5 pH units.

Upon addition of an additive, the solubility of MPA and phosphate decreased in supercritical water. Based on the concentration of MPA and phosphate found at supercritical conditions, the solubility of these compounds is approximately, 4,500 mg/L and 30 mg/L, respectively, in the absence of an additive; and 550 mg/L and 10 mg/L, respectively, in the presence of NaOH.

The additive had little effect on the conversion of methanol at all three oxygen concentrations tested. This is most likely due to the fact that methanol undergoes very little hydrolysis.

Inclusion of an additive for alteration of solubilities of intermediate products under supercritical or near critical conditions to effect the increased production of a product is an important aspect of the present invention. The solubilities of exemplary inorganic salts and metal oxides in water are given in Table 1 for standard temperature and pressure conditions, and in Table 2 for supercritical water conditions.

TABLE 1

Properties of Selected Salts and Oxides In Water at Standard Temperature and Pressure

| Compound | Melting Point (°C.) | Density (g/cm³) | Solubility (mg/L) | (@°C.) |
|---|---|---|---|---|
| NaCl | 801 | 2.165 | 391,200 | (100) |
| NaHCO$_3$ | 270 | 2.159 | 164,000 | (60) |
| Na$_2$CO$_3$ | 851 | 2.533 | 455,000 | (100) |
| Na$_2$SO$_4$ | 884 | 2.680 | 283,000 | (100) |
| Mg(OH)$_2$ | 350 | 2.360 | 40 | (100) |
| NaNO$_3$ | 306.8 | 2.261 | 921,100 | (25) |
|  |  |  | 1,800,000 | (100) |
| Na$_2$B$_4$O$_7$ | 741 | 2.367 | 87,900 | (40) |
| Na$_3$PO$_4$.12H$_2$O | 73.3–76.7 | 1.62 | 1,570,000 | (70) |
| Na$_2$HPO$_4$.12H$_2$O | 35.1 | 1.52 | 874,000 | (34) |
| NaH$_2$PO$_4$.2H$_2$O | 95 | 2.066 | 1,170,000 | (80) |
| NaOH | 318.4 | 2.130 | 420,000 | (0) |
| KOH | 360.4 | 2.044 | 1,070,000 | (15) |
|  |  |  | 1,780,000 | (100) |
| SiO$_2$ (Quartz) | 1610 | 2.660 | Insoluble |  |
| Al$_2$O$_3$ | 2072 | 3.965 | Insoluble |  |
| α-Al$_2$O$_3$ | 2015 | 3.970 | 0.98($^1$) |  |
| γ-Al$_2$O$_3$ | (1) | 3.5–3.9 | Insoluble |  |

(1) transition to α-Al$_2$O$_3$

TABLE 2

Solubilities of Selected Salts and Oxides in Supercritical Water

| Compound | Pressure (MPa) | Temperature (°C.) | Solubility (mg/L) |
|---|---|---|---|
| NaCl | 27.6 | 500 | 304 |
|  | 25.0 | 450 | 200 |
|  | 30.0 | 500 | 200 |
|  | 20.0 | 450 | 63 |
|  | 29.8 | 408 | 824 |
|  | 29.8 | 509 | 299 |
| Na$_2$SO$_4$ | 27.4 | 350 | 70,000 |
|  | 30.0 | 450 | 0.02 |
|  | 29.8 | 407 | 136 |
| NaHCO$_3$ | 29.8 | 509 | 86 |
| CaCO$_3$ | 24.0 | 440 | 0.02 |
| Mg(OH)$_2$ | 24.0 | 440 | 0.02 |
| NaNO$_3$ | 27.6 | 450 | 991 |
|  | 27.6 | 475 | 630 |
|  | 27.6 | 500 | 540 |
| SiO$_2$ | 34.5 | 400 | 637 |
|  | 34.5 | 500 | 216 |
|  | 25.0 | 450 | 55 |
|  | 30.0 | 450 | 160 |
| CuO | 31.0 | 620 | 0.015 |
|  | 25.0 | 450 | 0.010 |

A comparison of data presented in Tables 1 and 2 demonstrate the dramatic decrease in solubility for inorganic compounds under SCW conditions versus standard conditions.

The lowest mass of soluble chromium and iron was observed in tests conducted with additives during hydrolysis and partial oxidation tests described in Example 3. In the presence of additives or excess oxygen, this decrease in soluble chromium and iron is most likely due to the formation of insoluble chromium and iron species, such as Cr$_2$O$_3$, Cr(OH)$_6$, CrPO$_4$, Fe$_2$O$_3$, FeCr$_2$O$_4$, or Fe(OH)$_2$; the formation of a protective layer on the reactor walls; or the adsorption of chromium and iron species onto precipitates which are insoluble at normal conditions.

The recovery of ammonia is presented in Example 4. The batch process described herein provides only an example of the methods of the present invention. Continuous flow apparatus as described in U.S. Ser. Nos. 08/003,240, 08,142, 777, 08/184,951 and 08/191,390, incorporated by reference herein, may be used to accomplish the controlled hydrothermal processes of the present invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. Unless mentioned otherwise, the techniques employed herein are standard methodologies well known to one of ordinary skill in the art.

EXAMPLE 1

CONVERSION OF DMMP

The present example describes the oxidation of DMMP at different oxygen concentrations in supercritical water. DMMP serves as a model for organic wastes or byproducts containing a heteroatom.

Figure 2:
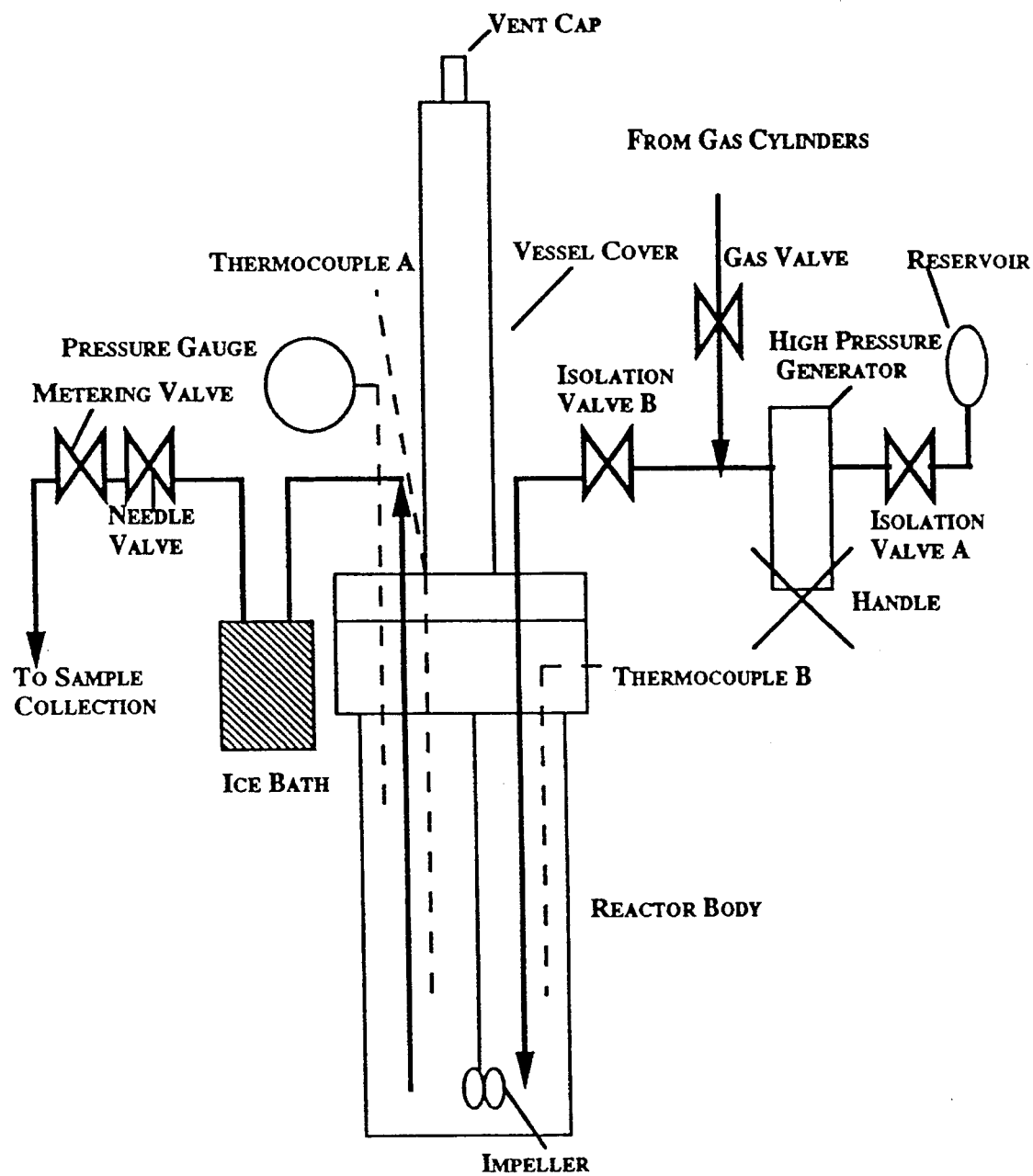
FIG. 2 shows the reactor set-up of the present invention.

An autoclave bolted closure reactor vessel with a capacity of 300 mL, shown in FIG. 2, was used to conduct batch tests. This reactor was equipped with sampling and injection ports. The sample volume was loaded initially into the reactor and heated to achieve the desired density. Since the contaminant of concern was injected after the desired test temperature and pressure was achieved, sample results were not subject to experimental error due to heat-up inconsistencies. Samples could be collected while the reactor was operating at supercritical water conditions. This feature enabled the collection of multiple samples at different residence times. Both gas-phase and liquid-phase samples could also be collected simultaneously.

The body of the autoclave was rated for 37.2 MPa (5400 psi) and was equipped with a pressure gauge, a safety rupture disk, and a port through which a thermocouple (B) was installed. The cover of the autoclave accommodated a cooling coil and sampling line; an injection line; a thermowell (thermocouple A); and an impeller which was driven magnetically by a seal-less Magdrive unit. The impeller was set at 750 rpm. A furnace which fit over the body of the autoclave provided the heat source. The cover of the reactor was bolted to the body with six B-16 alloy cap screws. A stainless steel gasket was used as a seal between the cover and the body of the reactor.

The injection system consisted of a HIP, Teflon-lined, high-pressure generator, rated for 34.5 MPa (5000 psi); a reservoir; a pressure gauge; a check valve; and two isolation valves. The generator was operated manually by rotating a handle. An inverted flask, 125-mL capacity, served as the reservoir, and was connected via Teflon tubing to isolation valve A. To connect the remaining components of the system, stainless steel tubing ID 0.089 cm (0.035 in.) was used. A check valve was installed between the generator and isolation valve B to prevent back flow from the reactor into the generator. The volume generated by one rotation of the generator handle was calibrated at room temperature under high pressure conditions. This volume was 0.65 mL/rotation. Pressure increases resulting from the additional volume injected during actual tests indicated that the calibrated volume was accurate within ±10%.

Once the reactor reached the desired temperature and pressure, a pressure equal to the pressure in the reactor was generated in the injection system. Isolation valve B was opened and the generator handle was rotated five times to deliver 3.25 mL of DMMP to the reactor. Then, isolation valve B was closed and the stop watch started at t=0. By making the injection in five rotations, the initial DMMP solution was delivered to the reactor in a short time relative to the residence time of the samples and the concentration of the initial solution was not made unnecessarily concentrated.

Gas-phase samples were collected by fastening a 60-mL plastic syringe using thin tygon tubing to the vent line that was pierced through permanent vial cap. Liquid-phase samples were collected simultaneously into a 15-mL sample vial screwed into the vial cap. After a residence time of five minutes, the sampling valve was opened slowly and liquid condensate was collected in the glass vial while the gas sample filled the plastic syringe. Within 20 seconds, 50 mL of gas was collected in the syringe, removed and clamped while the sampling valve was left open to collect approximately 15 mL of liquid-phase sample.

After samples were collected, the chilled water was turned on to initiate reactor cool down. Once the reactor was cooled, the final pressure and temperature were recorded and the excess pressure within the reactor was either released or collected for analysis. A 100-mL rinse of hot deionized water was then used to rinse the inside of the reactor cover and body to dissolve any phosphates which precipitated during the reaction. This rinseate was collected for analysis.

Conversion of DMMP at Different Oxygen Concentrations. Initial tests were conducted to determine the by-product distribution of DMMP at different oxygen concentrations in supercritical water. Hydrolysis (no oxygen in system), partial oxidation (17.6% of stoichiometric oxygen demand in system) and oxidation (>100% stoichiometric oxygen demand in system) tests were performed. No additive was used in this example. Methanol, MPA, phosphate, and carbon dioxide were detected in significant quantities; no residual DMMP was detected. Carbon monoxide and methane were not detected in quantifiable amounts. The fraction of carbon and phosphorus in each by-product was calculated based on the mass of carbon or phosphorus in each by-product divided by the total mass of carbon or phosphorus in all by-products.

The recovered total mass of carbon and phosphorus calculated for each run was 25% higher on average than the initial carbon mass and 12% lower that the initial phosphorus mass. Errors in mass balance calculations were mainly procedural. The error in the carbon mass balance was based in part on the uncertainty of the initial concentration of DMMP due to dilution within the injection system and on the graphite bearing in the reactor shaft. This bearing was largely composed of carbon and the wear provided an additional source of carbon. Controls were conducted to quantify the amount of carbon added by the bearing and the data was adjusted accordingly. The low recovery of phosphorus was due to difficulties in retrieving precipitated phosphorus in the form of phosphates or MPA from reactor internals. As rinsing techniques improved over the course of the study, the percent recovery of phosphorus increased from 67% to 91%.

Figure 3:
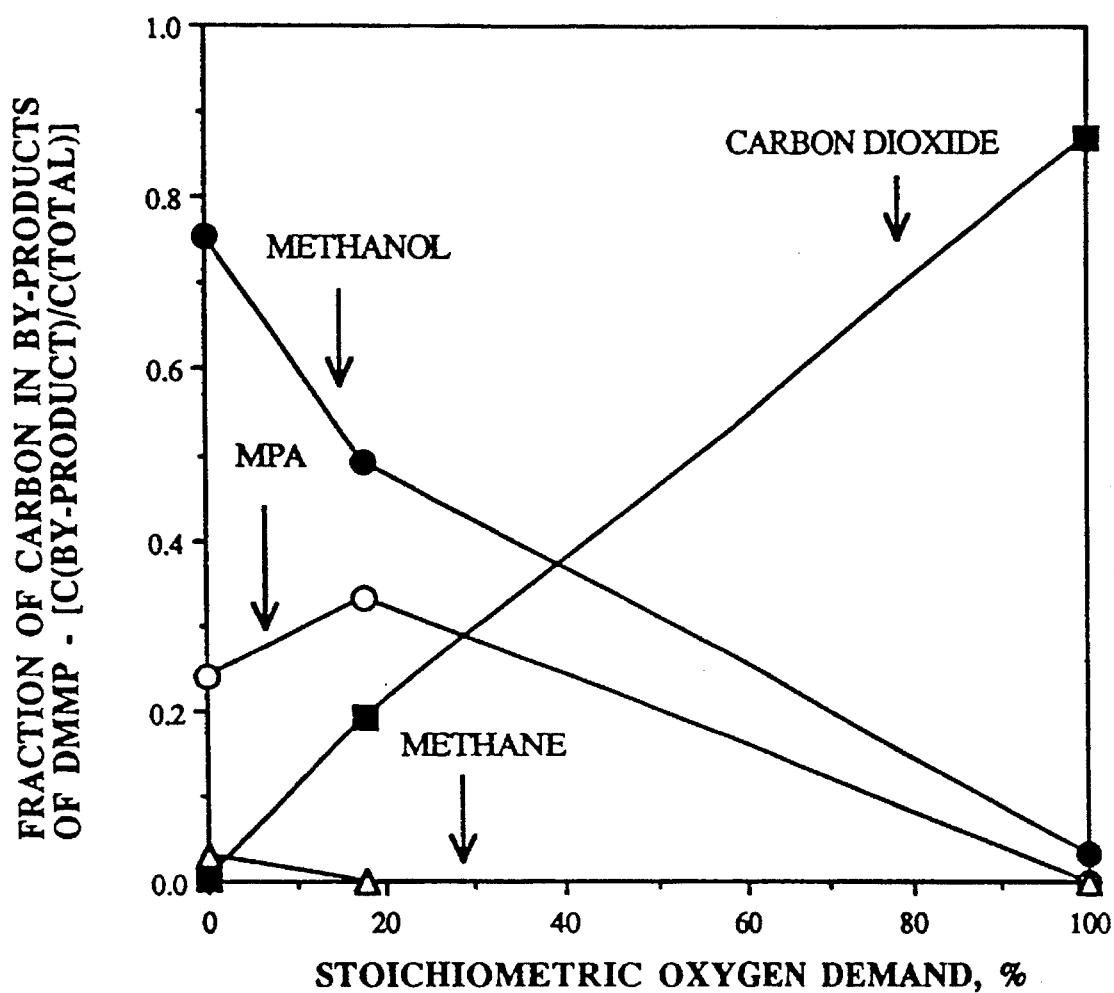
FIG. 3 shows the fraction of carbon in by-products of DMMP in the absence of additives after five minute residence time.
Figure 4:
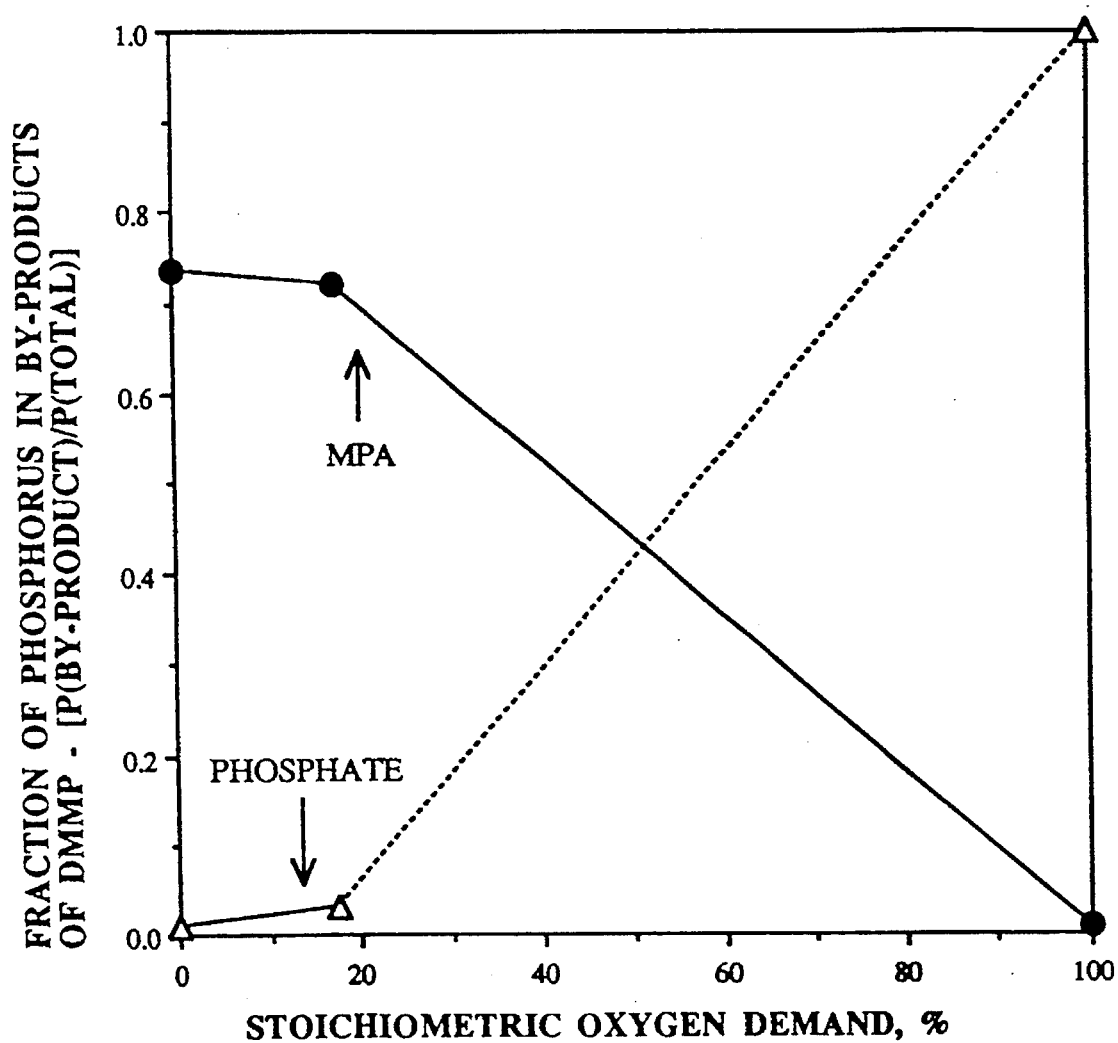
FIG. 4 shows the fraction of phosphorus in by-products of DMMP in the absence of additives after five minute residence time.
Figure 5:
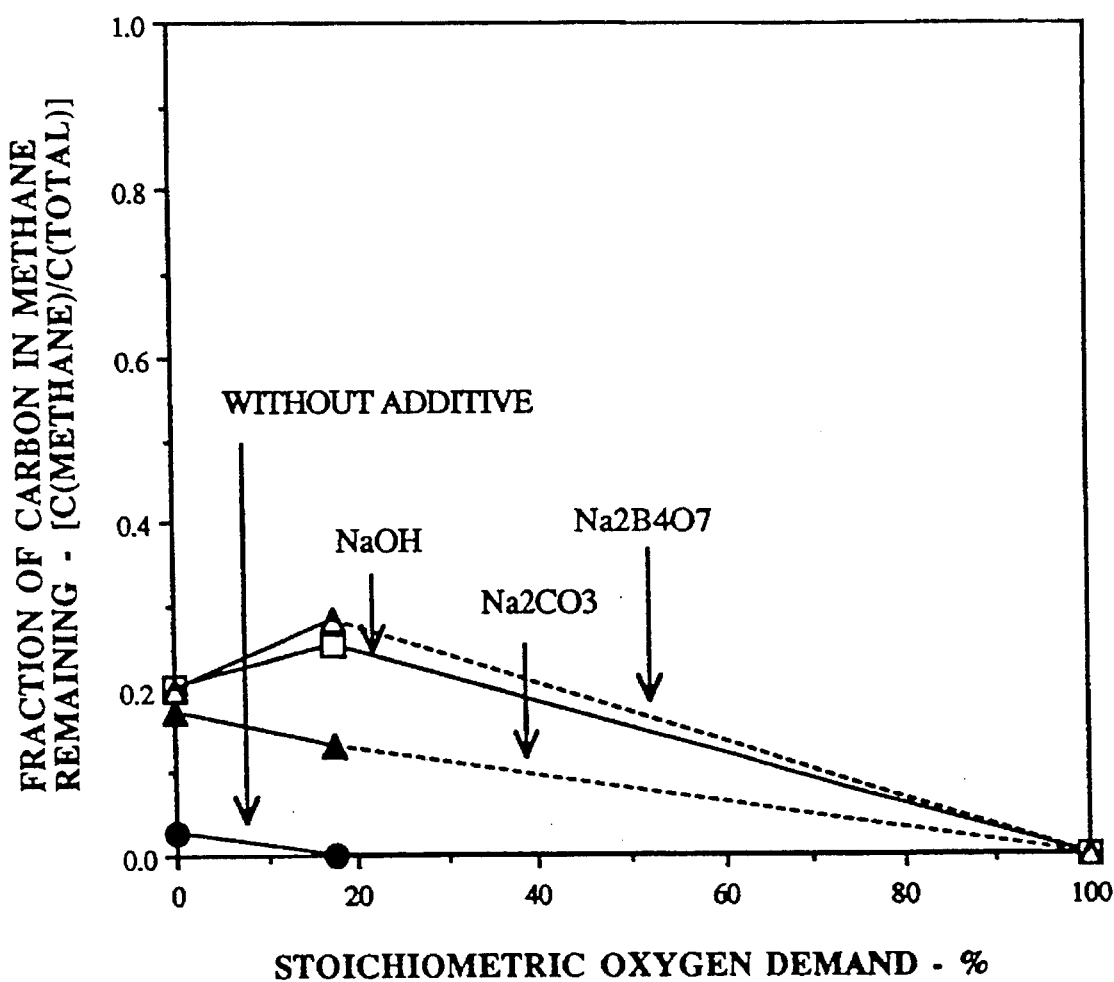
FIG. 5 shows the fraction of carbon in methane in the presence of different additives after five minute residence time.
Figure 6:
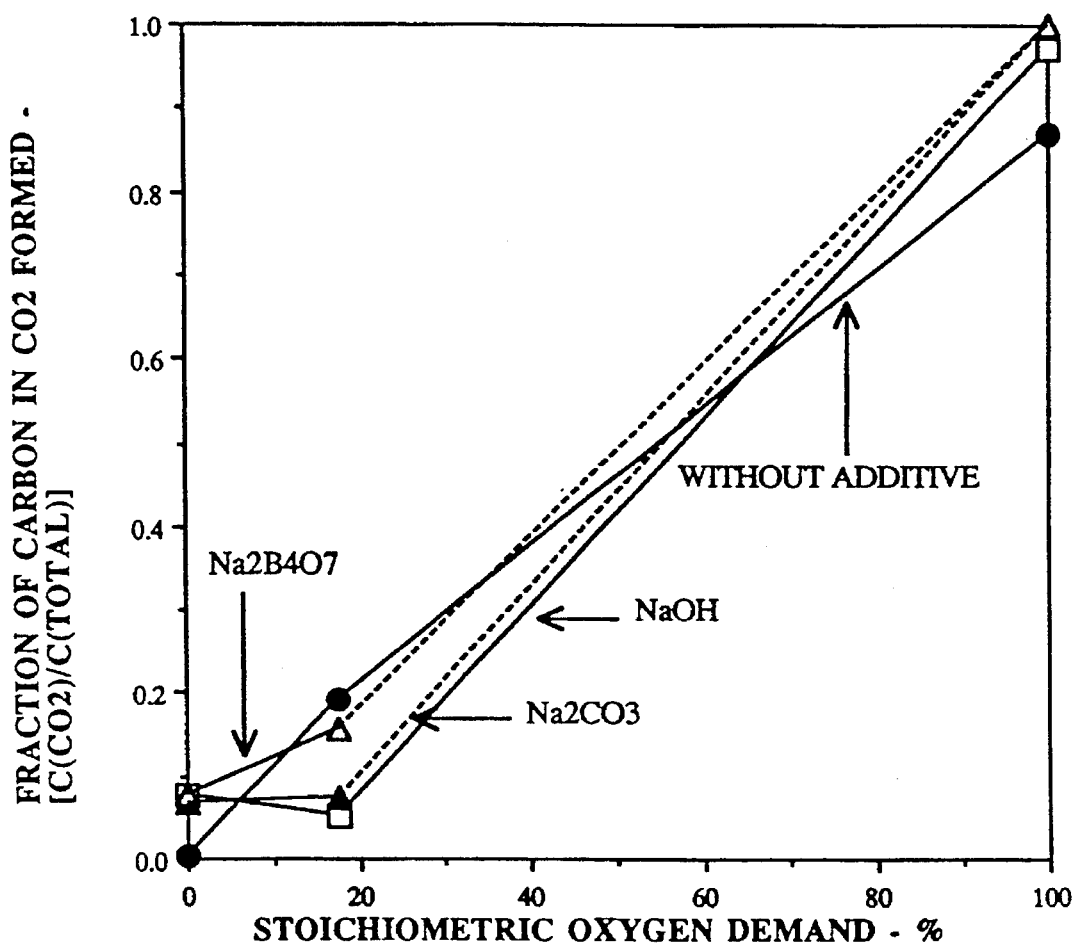
FIG. 6 shows the fraction of carbon in $CO_2$ formed in the presence of different additives after five minute reactor residence time.
Figure 7:
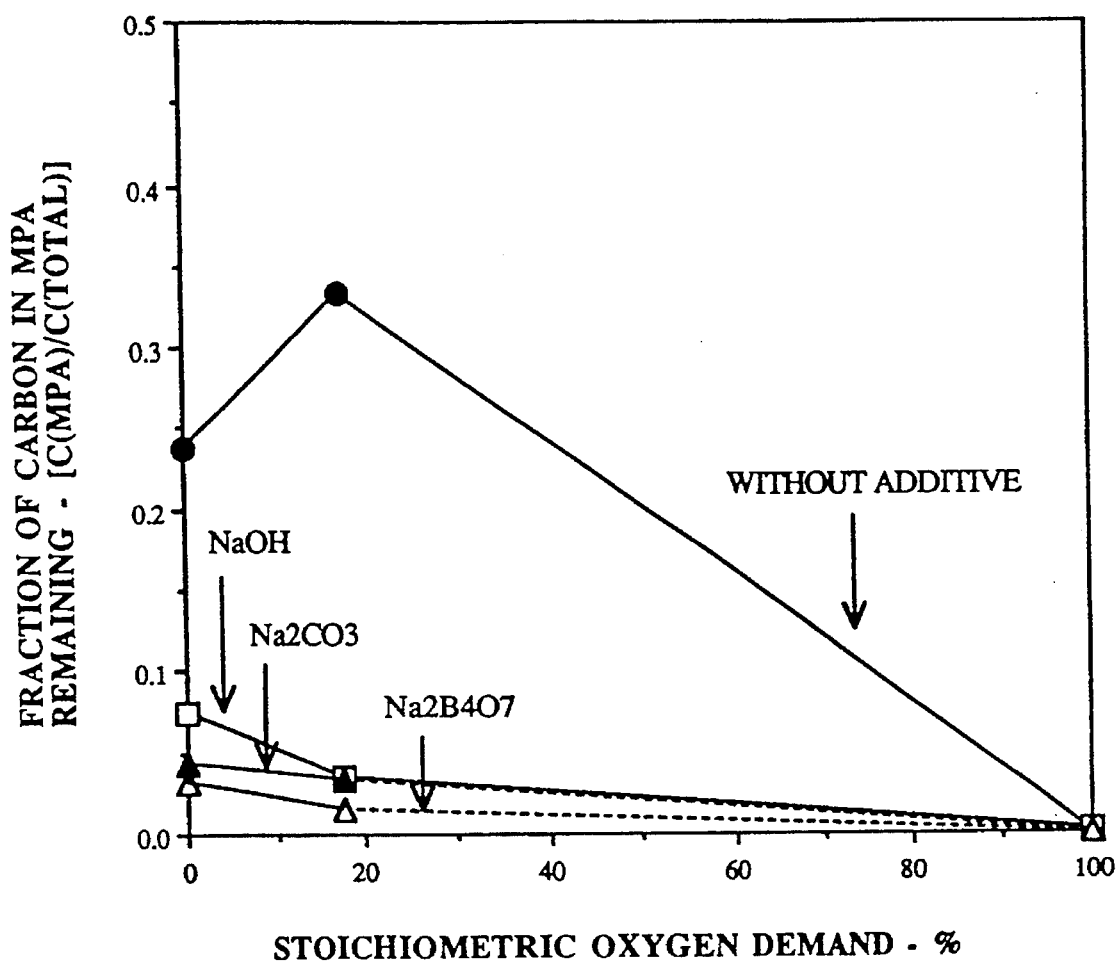
FIG. 7 shows the fraction of carbon in MPA remaining in the presence of different additives after five minute reactor residence time.
Figure 8:
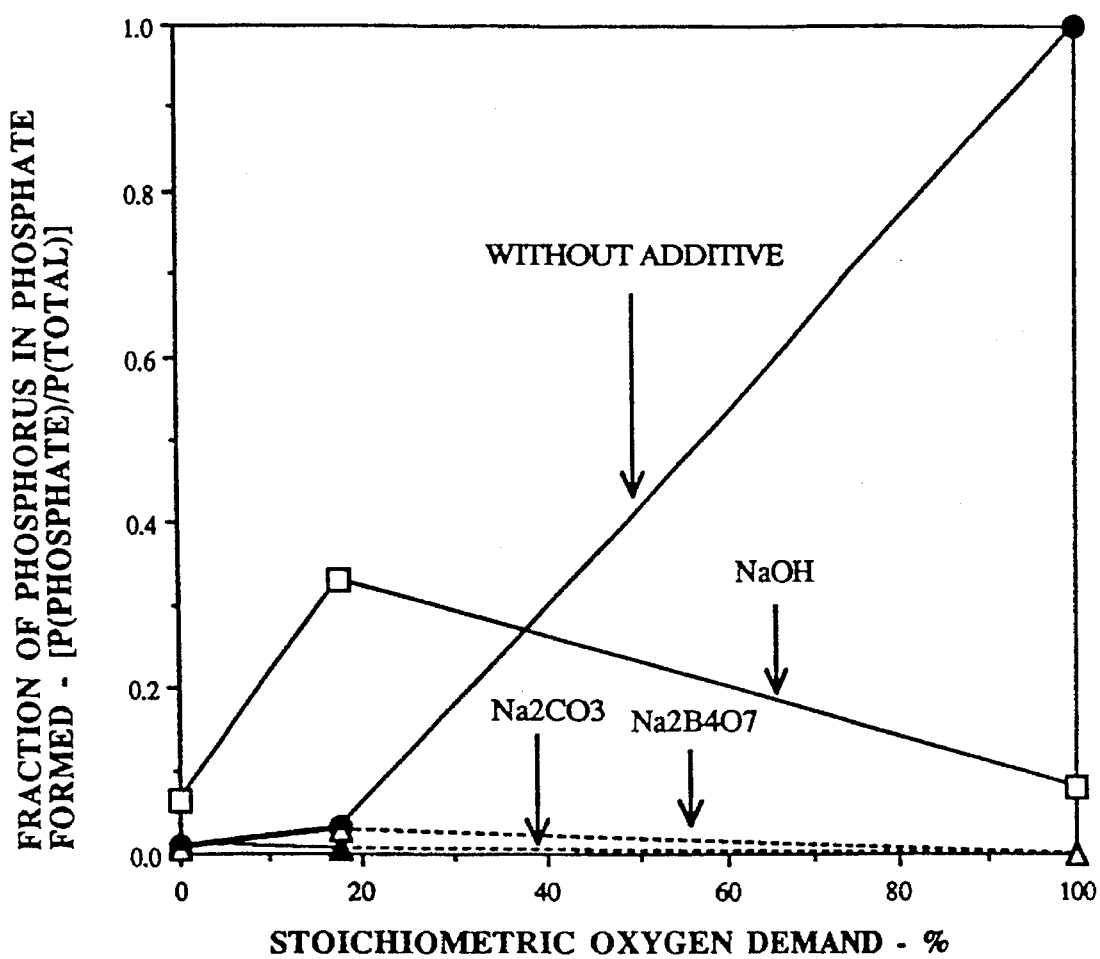
FIG. 8 shows the fraction of phosphorus in phosphate formed in the presence of different additives after five minute reactor residence time.
Figure 9:
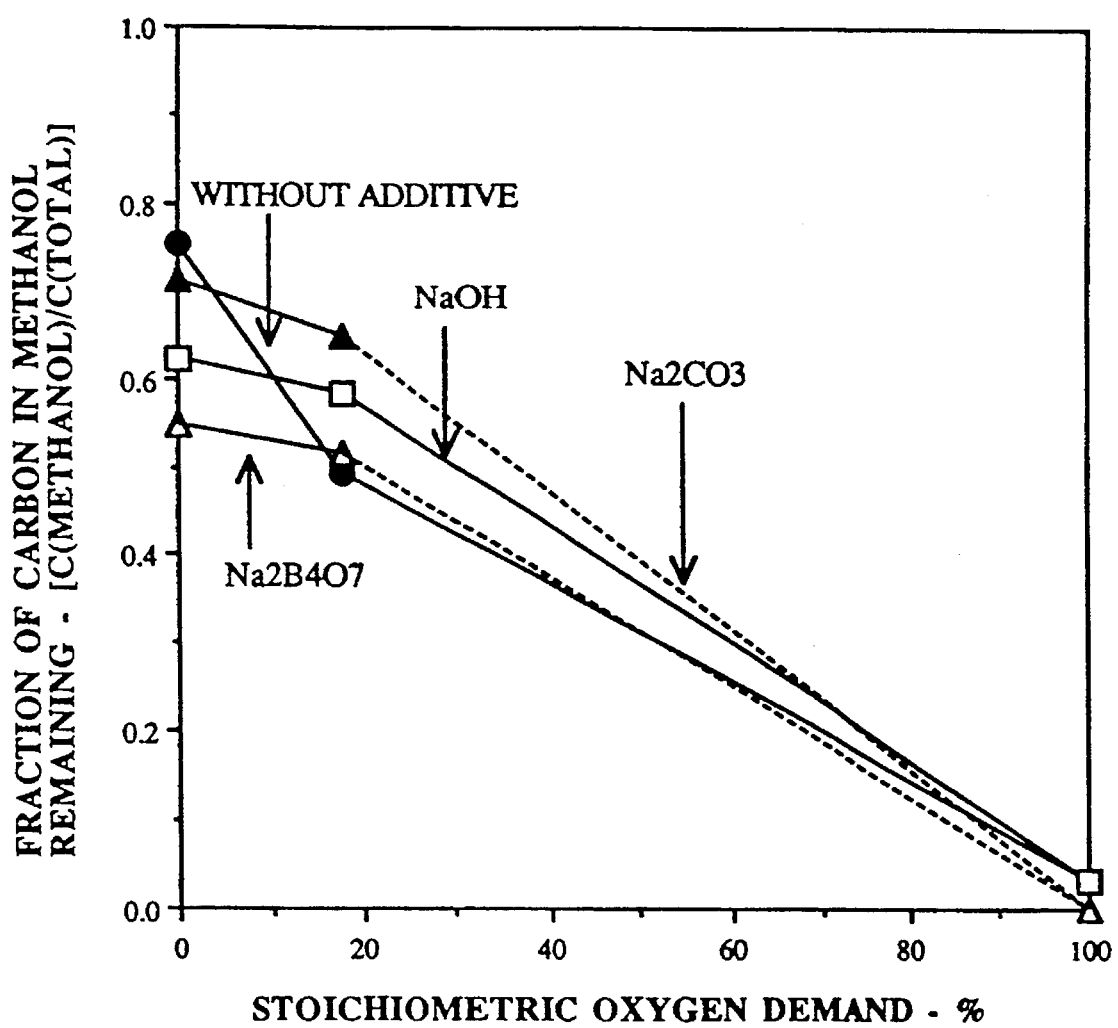
FIG. 9 shows the fraction of carbon in methanol remaining in the presence of different additives after five minute reactor residence time.

FIGS. 3 and 4 show the fraction of carbon and phosphorus in each of the by-products as a function of oxygen concentration. Data reported at 100% of the stoichiometric oxygen demand actually were conducted in the presence of sixteen times the stoichiometric oxygen demand. As the concentration of oxygen increased in the reactor, more by-products were transformed to oxidation products. This reaction is indicated by the increase in $CO_2$ concentration. Carbon monoxide and carbon dioxide are by-products of oxidation only while methane is a by-product of hydrolysis only as shown in FIG. 1. By-product formation in the gas phase, therefore, is indicative of the reaction pathways proceeded under different conditions. During hydrolysis tests, reaction mechanisms were expected to follow those described in equations A and B of FIG. 1. Methanol and MPA were produced in the greatest quantities during these tests. These compounds are hydrolysis by-products as indicated in equation A. Only small amounts of methane and phosphate were detected, indicating that hydrolysis of MPA (shown in equation B) was not significant.

As the oxygen concentration increased, the amount of $CO_2$ and phosphates increased, while methanol and MPA decreased. Methane was not detected during these runs in significant concentrations. The by-product distributions at the various oxygen concentrations suggest that methanol and MPA were depleted via oxidation reaction pathways as described in equations C and F. The increase in phosphate concentration corresponded to the oxidation of MPA. Although phosphates were also an end-product of MPA hydrolysis, no detectable amount of methane was formed indicating that this reaction pathway was not significant.

EXAMPLE 2

CONVERSION OF DMMP AND PRODUCTION OF METHANE IN THE PRESENCE OF ADDITIVES

The present example describes the effect various additives have on the oxidation of DMMP at different oxygen concentrations. In particular, the present example demonstrates the utility of including additives in the production of methane under SCWO conditions. The reaction of methylphosphonic acid (MPA) under supercritical conditions water to form phosphoric acid and methane is depicted as reaction (B) in FIG. 1.

Fourteen tests were conducted to determine the by-product distribution of DMMP during SCWO at different oxygen concentrations in the presence of additives. Test conditions and procedures were the same as described in Example 1. Additive concentrations were based on achieving a 1:1 molar ratio of $Na^+$ ions to DMMP. Based on an initial concentration of DMMP of 10,000 mg/L, the initial concentrations of each additive were 3,224 mg/L for NaOH, 4,271 mg/L for $Na_2CO_3$ and 15.4 g/L for $Na_2B_4O_7$ (as $Na_2B_4O_7 \cdot 10H_2O$).

FIGS. 5 through 9 show the fraction of carbon and phosphorus in each by-product as a function of oxygen concentration after five minutes of reactor residence time. Results at each condition were compared to those obtained without the additive at the same condition. The presence of the additive supported methane production at lower oxygen concentrations, suppressed the fraction of MPA remaining at low oxygen concentrations, and suppressed the fraction of phosphate remaining in solution at high oxygen concentrations. A higher fraction of $CO_2$ was observed during hydrolysis runs in the presence of the additive while $CO_2$ generation was suppressed during partial oxidation runs. In the presence of additives, during oxidation tests, $CO_2$ generation was increased slightly. The fraction of methanol remaining was not significantly affected by the presence of the additive during oxidation tests.

Sodium phosphate salts are highly insoluble in supercritical water. The precipitation of the phosphate pulls the reaction in the direction of producing more phosphate and also more methane. The solubility of these salts in supercritical water may be only a few parts per million. Therefore, during the hydrolysis of MPA, phosphoric acid can be precipitated effectively from the reaction phase.

Increased methane production during the hydrolysis and partial oxidation tests in the presence of additives indicates support of hydrolysis reaction pathways. As shown in equation B of FIG. 1, MPA hydrolysis results in the formation of phosphate and methane. This reaction pathway was more readily supported upon the addition of sodium hydroxide. Without being bound by theory, there are two possible explanations for the observed support of the hydrolysis pathway. First, properties of supercritical water are altered upon addition of ionic species. Previous studies have shown the amount of hydrolysis by-products to increase in supercritical water upon addition of ionic species (Huppert et al., 1989; Weast and Astle, 1982). This phenomenon, as noted in previous studies, was due to an increase in the dielectric constant or polarity of the solution. Such a solution was more supportive of heterolytic reactions. These previous tests were conducted near the critical point of water at densities of about 0.3 g/cm³, densities higher than those tested here. As proposed in other studies at lower densities, hydrolysis may be accomplished by the addition of $H_2O$ as a nucleophile in homolyric conditions (Klein et al., 1990; Lee and Gloyna, 1990). This may serve as one hydrolysis pathway. However, significant hydrolysis was not observed in the absence of the additives which suggests that heterolytic pathways were established upon use of the additive.

In addition, hydrolysis in a heterolytic environment may be catalyzed via the addition of hydronium or hydroxide ions. Table 1 shows that the pH values after a five minute reactor residence time were slightly higher in the presence of additives than without additives. This slight increase in pH suggests that higher methane concentrations may be due to the presence of increased hydroxide ion concentration which may have catalyzed the MPA hydrolysis pathway.

TABLE 3

SAMPLE pH BEFORE SCWO, AFTER FIVE-MINUTE REACTOR RESIDENCE TIME, AND AFTER REACTOR COOL DOWN

| | pH | | |
|---|---|---|---|
| Test Condition | Initial | 5 Min. Reactor Resid. Time | After Reactor Cool Down |
| no additive, hydrolysis | 4 | 1.6 | 2.5 |
| no additive, partial oxidation | 4 | 1.6 | 3.6 |
| no additive, oxidation | 4 | 1.9 | 2.2 |
| NaOH, hydrolysis | 12.3 | 2.1 | 5.3 |
| NaOH, partial oxidation | 12.3 | 2.2 | 6.0 |
| NaOH, oxidation | 12.3 | 3.6 | 5.0 |
| $Na_2CO_3$, hydrolysis | 11 | 2.5 | 6.0 |
| $Na_2CO_3$, partial oxidation | 11 | 2.4 | 6.7 |

TABLE 3-continued

SAMPLE pH BEFORE SCWO, AFTER FIVE-MINUTE REACTOR RESIDENCE TIME, AND AFTER REACTOR COOL DOWN

| | pH | | |
|---|---|---|---|
| Test Condition | Initial | 5 Min. Reactor Resid. Time | After Reactor Cool Down |
| $Na_2B_4O_7$, hydrolysis | 9 | 2.8 | 7.0 |
| $Na_2B_4O_7$, partial oxidation | 9 | 3.2 | 7.3 |

Table 3 shows the pH of samples collected after five minutes of reactor residence time and samples collected after reactor cool down. The pH of each sample was measured within one hour of sample collection. The presence of the additive affected the pH of the sample collected after a five minute reactor residence time only slightly. Since the pH of the initial solution had increased upon addition of the additive, it was expected that the pH of the sample collected at supercritical conditions would also increase. However, the effect was only slightly obvious due most likely to the precipitation of the additives at supercritical conditions. After reactor cool down, the pH of samples collected after cool down increased in the presence of the additive. The pH increase which occurred between the sample collected after five minutes reactor residence time and after reactor cool down was a result of the dissolution of precipitated additive. It is believed that sodium hydroxide, sodium carbonate and sodium borate dissolved after reactor cool down and neutralized the acidic solution which was observed after the five minute reactor residence time.

Another reason for increases in methane production observed in the presence of the additives may be related to the solubilities of MPA and phosphate. Solubility tests were conducted to determine the solubility of MPA and phosphates with and without NaOH. As was observed in solubility tests conducted without additives, phosphate and MPA precipitated out of solution at supercritical water conditions. These solubilities decreased, in the presence of an additive as shown in the following Table 4.

TABLE 4

CONCENTRATIONS OF MPA AND $H_3PO_4$ IN THE PRESENCE OF VARIOUS ADDITIVES

| Additive | Temperature (°C.) | Pressure (MPa) | MPA (mg/kg solution) | $H_3PO_4$ (mg/kg solution) |
|---|---|---|---|---|
| None | 455.9 | 26.6 | 4500 | |
| None | 454.5 | 29.3 | | 30 |
| NaOH | 448.7 | 27.9 | 550 | |
| NaOH | 457.5 | 29.3 | | 10 |
| $Na_2CO_3$ | | | 1400 | |
| $Na_2CO_3$ | | | | 22 |
| $Na_2B_4O_7$ | | | 720 | |
| $Na_2B_4O_7$ | | | | 30 |

TABLE 5

COMPARISON OF CONCENTRATION OF PHOSPHATE
AND MPA DETECTED IN SOLUBILITY TESTS AND
DMMP TESTS WITH AND WITHOUT ADDITIVES

|  | Phosphates (mg/L) | MPA (mg/L) |
| --- | --- | --- |
| Without Additives | | |
| Solubility Concentration | 30 | 4,500 |
| DMMP Hydrolysis Concentration | 45 | 4,700 |
| DMMP Partial Oxidation Concentration | 4 | 6,200 |
| DMMP Oxidation Concentration | 4,000 | 20 |
| With NaOH | | |
| Solubility Concentration | 10 | 550 |
| DMMP Hydrolysis Concentration | 300 | 1,540 |
| DMMP Partial Oxidation Concentration | 350 | 770 |
| DMMP Oxidation Concentration | 300 | <25 |

Table 5 shows the measured concentrations of MPA and phosphate measured with and without NaOH as well as MPA and phosphate concentrations detected during DMMP tests conducted with and without NaOH. As was the case without the additive, concentrations observed during DMMP tests were often greater than the solubility determined due to the additional agitation experienced during these tests. The impeller was slowed down considerably during solubility tests to allow for settling of precipitates. It is speculated that as phosphate precipitated out of solution, an equilibrium shift in MPA hydrolysis occurred, supporting further formation of phosphates. As phosphate was removed from solution, a greater driving force existed for the production of methane at low oxygen concentrations.

Methane may be easily recovered from the effluent at ambient conditions. Using adsorptive or membrane technologies, methane and other higher molecular weight alkanes may be separated from other gases such as $CO_2$, CO and water vapor. Reaction temperature, pressure, and type of additive may be optimized based on salt solubility salt-water phase behavior and reaction kinetics.

One skilled in the art would understand in light of the present disclosure that ethane, propane or butane or possibly higher hydrocarbons, and their isomers, for example, may be produced and recovered in a similar manner to the production and recovery of methane provided in the present example.

EXAMPLE 3

LESS CORROSION OCCURS IN THE PRESENCE OF ADDITIVES

The present example describes the effect of additives on corrosion products formed during SCWO.

Figure 10:
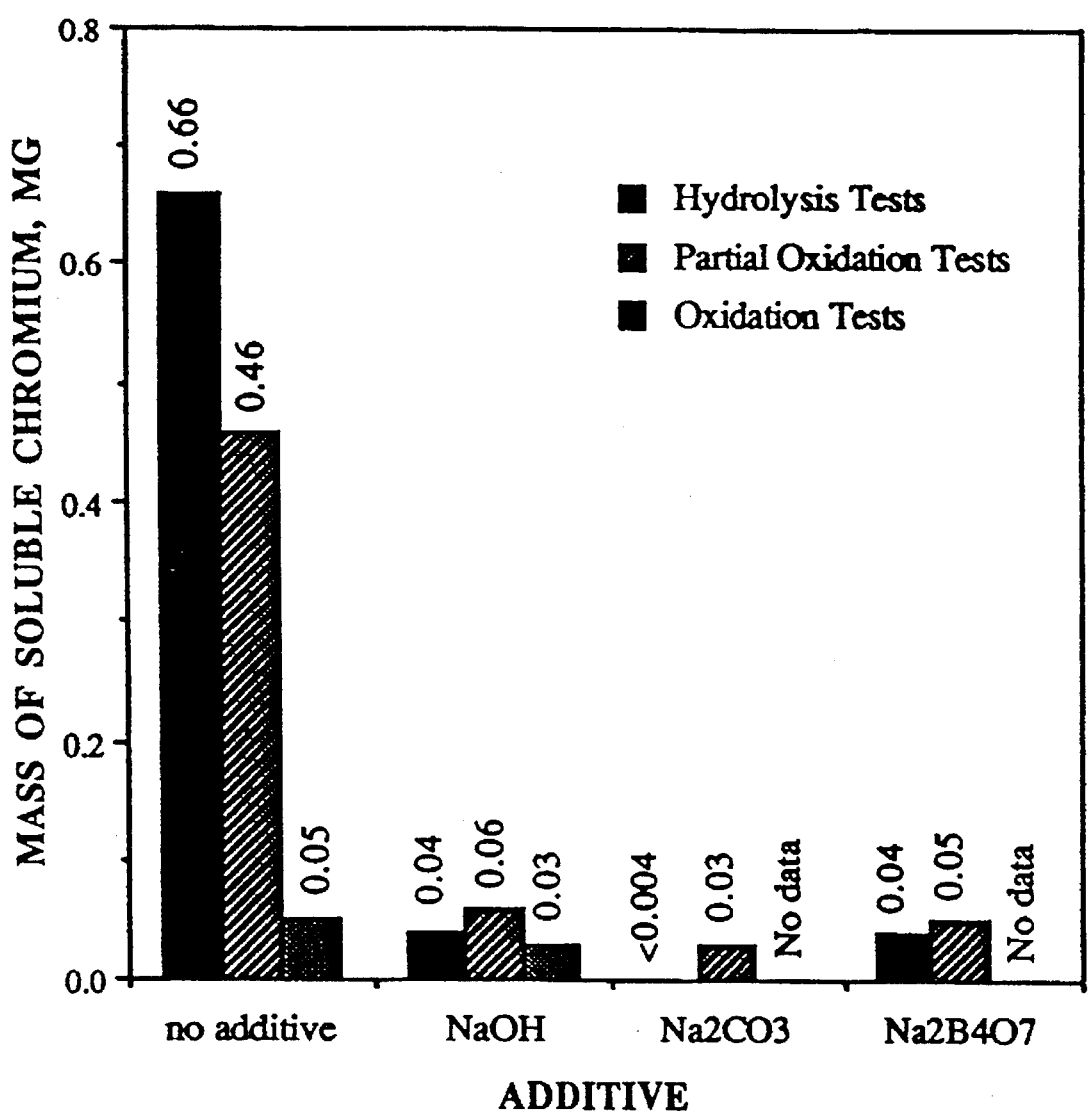
FIG. 10 shows the mass of soluble chromium in samples collected after reactor cool down.
Figure 11:
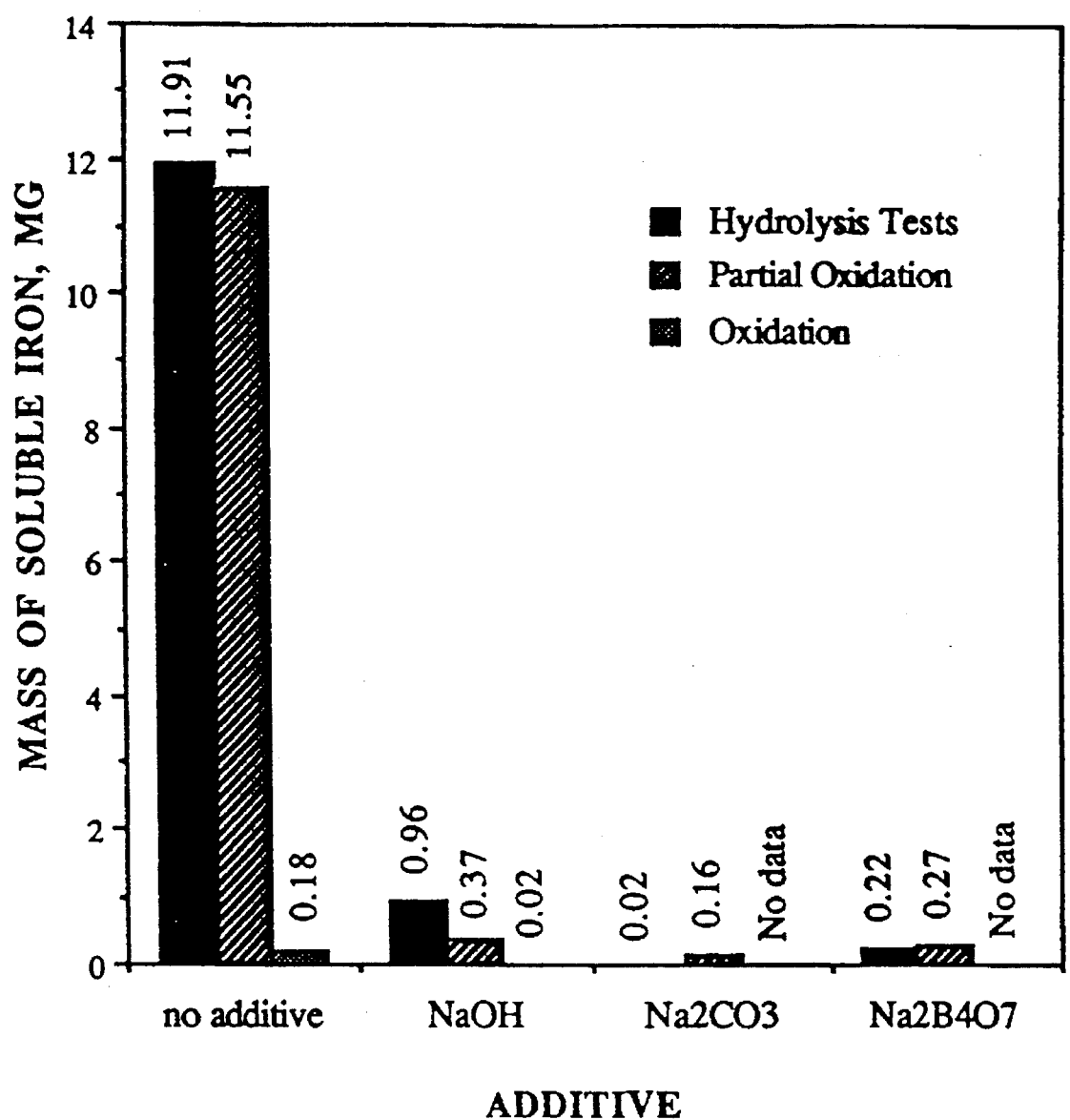
FIG. 11 shows the mass of soluble iron in samples collected after reactor cool down.

Samples collected after reactor cool down were analyzed for soluble chromium and iron. FIGS. 10 and 11 show the quantity of chromium and iron found in samples derived from tests conducted at three oxygen concentrations, with and without additives. Approximately twelve times more soluble chromium and iron were detected during hydrolysis and partial oxidation tests conducted without additives than any other test. Only a small percentage (between 1 and 10%) of the soluble chromium detected was in the hexavalent form.

Possible explanations for the elevated levels of chromium and iron in the hydrolysis and partial oxidation runs conducted without additives include the following. Insoluble corrosion products may be formed in the presence of the additive, decreasing the amount of soluble iron and chromium in the reactor. Chromium may react with water, hydroxyl ions, or phosphates to form insoluble solids such as $Cr(OH)_2$, $Cr_2O_3$, $Cr(OH)_6$ and $CrPO_4$. Iron may also form insoluble solids such as, $Fe_2O_3$, $FeCr_2O_4$, and $Fe(OH)_2$. These insoluble solids may have formed during heat up, at supercritical conditions, or during reactor cool down in the presence or absence of the additive. Oxide and hydroxide formation may have increased, however, in the presence of the additives or oxygen. Upon addition of the additive, sodium chromate compounds such as $Na_2CrO_8$, $Na_2Cr_2O_7$, or $Na_2CrO_8$, or sodium ferrite, $Na_2Fe_2O_4$ may also have formed. Sodium chromate compounds are relatively soluble and sodium ferrite decomposes readily (Weast and Astle, 1982). After reactor cool down, depending on the total amount of chromium corroded from the reactor walls, it would be expected that most sodium-chromium precipitates would dissolve since likely concentrations of sodium-chromium precipitates were below the solubility of these compounds. Therefore, even if chromium were removed from the supercritical solution through precipitation with sodium, it still would have been detected after reactor cool down since it would have dissolved at normal conditions. Because of this, it can be assumed that the formation of sodium-chromium precipitates was not responsible for the removal of chromium from solutions which contained additives during hydrolysis and partial oxidation runs. Rather, chromium and iron combined with oxides or hydroxyl ions which were provided upon additive or oxygen addition.

Less corrosion may have taken place in the presence of additives during hydrolysis and partial oxidation tests due to the formation of a protective layer. The formation of insoluble solids may have acted as a protective layer along the reactor internals, preventing additional corrosion. Precipitates were visible after the reactor had cooled and was opened. Since the solubilities of these solids in supercritical water are not known, it is difficult to speculate which solids may have acted in this capacity. However tests, conducted previously in different types of steel at 160° C., indicated that the addition of phosphoric acid to hot formaldehyde solutions reduced corrosion due to the formation of a protective $CrPO_4$ and $Cr_2O_3$ layer (Gorchakov et al., 1990). In addition, it has been observed that phosphate and MPA experience decreased solubilities in the presence of additives. These ions may have combined with sodium ions to form a protective layer of sodium phosphate or sodium methyl phosphonate.

Lower levels of soluble chromium and iron quantities observed during tests conducted with additives or high concentrations of oxygen may have been due to the adsorption of these metals onto precipitates. Iron and chromium may have adsorbed onto insoluble precipitates and thereby were removed from solution. Most likely, this phenomenon occurred upon the formation of solids which were insoluble at normal conditions. Otherwise, these precipitates would have dissolved after reactor cool down, resulting in an increase in soluble chromium and iron levels. The adsorption of chromium in supercritical water was studied previously (Rollans and Gloyna, 1993). They found that trivalent chromium was more likely to be adsorbed onto colloidal matter in supercritical water as the pH of the solution increased. Since the pH of the solution after reactor cool down increased upon addition of the additives, their addition may have been responsible for decreased levels of chromium through adsorption.

EXAMPLE 4

PRODUCTION OF AMMONIA

The present example describes the recovery of ammonia from SCWO. Ammonia is a major and refractory intermediate compound in supercritical water oxidation of nitrogen-containing compounds, such as, amines (McBrayer et al., 1993), pyridine (Crain et al., 1993), and sludges (Shanableh, 1990; Tongdhamachart, 1991).

According to published kinetic data, the rate of ammonia oxidation in supercritical water becomes appreciable only at temperatures greater than 550° C. (Webley et al., 1991). Using these kinetic data, reactor residence times required to achieve various levels of ammonia conversion at temperatures ranging from 400° C. to 600° C. are calculated, as shown in Table 6.

TABLE 6

RATE OF AMMONIA OXIDATION IN SUPERCRITICAL WATER

| Temperature | Reactor Residence Time (min) Required to Achieve Specified Conversion | | | | |
|---|---|---|---|---|---|
| (°C.) | 9% | 90% | 99% | 99.9% | 99.99% |
| 400 | 774 | 18888 | 37775 | 56663 | 75551 |
| 450 | 111 | 2710 | 5421 | 8131 | 10842 |
| 500 | 20 | 500 | 1000 | 1500 | 2000 |
| 550 | 5 | 113 | 227 | 340 | 453 |
| 600 | 0.1 | 3 | 7 | 10 | 13 |

Calculations are based on the reported first-order reaction kinetic model in which pre-exponential factor=$3.16 \times 10^6$ (1/s), activation energy=157 (kJ/mol). Experiment pressure= 24.6 MPa, temperature range=530° C.–700° C. (Webley et al., 1991).

This table shows that below 450° C., a reactor residence time of at least two hours is required to convert 10% ammonia, indicating that ammonia is quite refractory at low-temperature regions for supercritical water oxidation.

Figure 12:
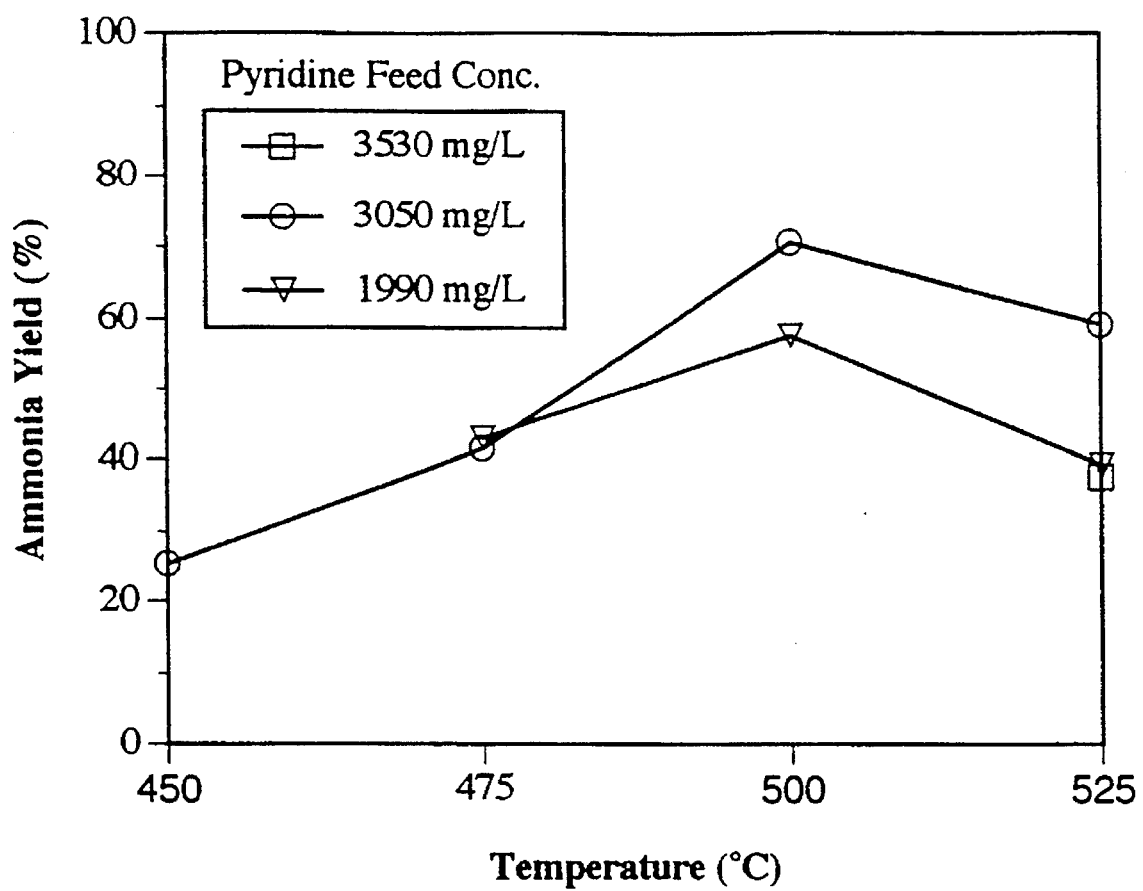
FIG. 12 shows ammonia yield in supercritical water oxidation of pyridine at 27.6 MPa. The residence times were as follows: 450° C., 9s; 475° C., 8s; 500° C., 7s and 525° C., 4s.
Figure 13:
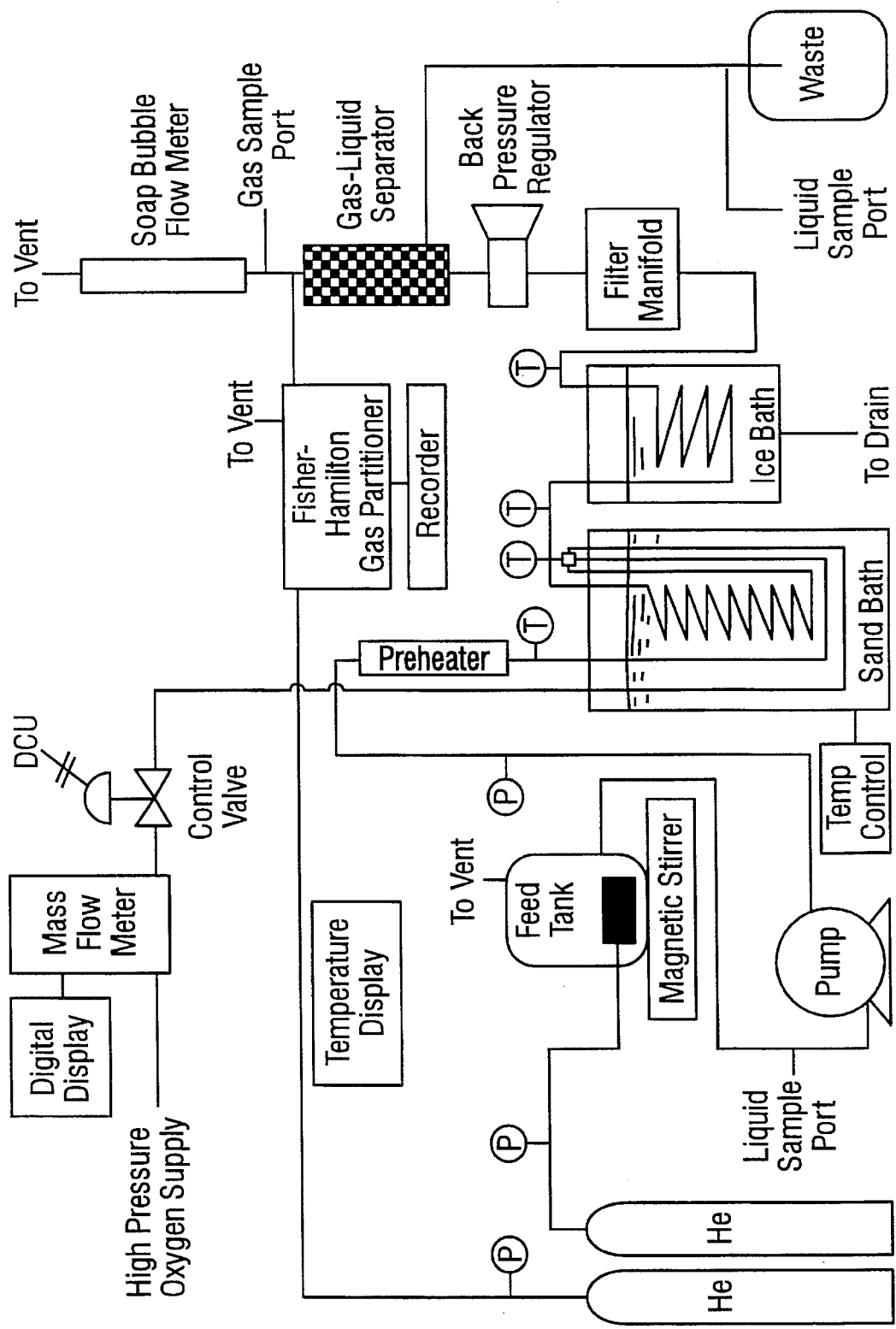
FIG. 13 shows a flow diagram of a laboratory scale, continuous-flow SCWO reactor system.

Significant ammonia production was observed in supercritical water oxidation of pyridine (Crain, 1993). The yield of ammonia in this process at selected test conditions (reaction temperature, reactor residence time, pyridine and oxygen feed concentrations) are shown in FIG. 12 and Table 7.

TABLE 7

AMMONIA YIELD IN SUPERCRITICAL WATER OXIDATION OF PYRIDINE

| Test No. | Reaction Temperature (°C.) | Residence Time (sec) | Pyridine Feed Conc. (mg/L) | Oxygen Concentration (mole/L) | Pyridine Conversion (%) | Ammonia Yield* (%) |
|---|---|---|---|---|---|---|
| 668 | 525 | 3.9 | 3530 | 0.014 | 53 | 35.1 |
| 661 | 527 | 3.8 | 3530 | 0.010 | 55 | 32.4 |
| 676 | 527 | 3.8 | 3530 | 0.020 | 68 | 45.6 |
| 541 | 522 | 6.6 | 3050 | 0.027 | 94 | 59.2 |
| 524 | 499 | 7.1 | 3050 | 0.031 | 75 | 70.6 |
| 542 | 474 | 7.8 | 3050 | 0.035 | 22 | 41.6 |
| 529 | 451 | 8.8 | 3050 | 0.038 | 6 | 25.4 |
| 513 | 522 | 6.6 | 1990 | 0.024 | 74 | 39.2 |
| 516 | 499 | 7.1 | 1990 | 0.026 | 66 | 57.7 |
| 525 | 475 | 7.8 | 1990 | 0.029 | 25 | 43.0 |

Experiment pressure = 27.6 MPa (Crain, 1993).
*Yield = (amount of nitrogen in ammonia)/(amount of nitrogen in converted pyridine).

The ammonia yield is based on the amount of nitrogen in ammonia divided by the amount of nitrogen in converted pyridine. For example, at 524° C., 75% of pyridine was converted and 71% of the converted pyridine became ammonia (Test No. 524). The remaining 29% of the converted pyridine was primarily nitrogen gas and nitrate. Pyridine conversion reduced significantly with decreasing temperature, whereas ammonia yield remained relatively constant. The foregoing examples indicate that if little or partial oxidation of nitrogen-containing compounds is allowed and process conditions of feed concentration, temperature and residence time are properly controlled, the reaction intermediate, ammonia, accumulates and is recoverable.

Hydrothermal processing also offers unusual options for ammonia separation and recovery from the reactor effluent. Although existing ammonia recovery technologies, such as stripping, may be considered, ammonia can be precipitated from supercritical water in the form of ammonium salts by adding anion donors, such as, acids and salts, in particular, an acid such as HCl.

The following references are incorporated in pertinent part by reference herein for the reasons cited above.

REFERENCES

Antal, M. J., et al., "Heterolysis and Homolysis in Supercritical Water," in Supercritical Fluids: Chemical Engineering Principles and Applications, T. G. Squires and M. E. Paulaitis, eds., ACS Symposium Series 329, American Chemical Society, Washington, 1987, pp. 77–86.

Baker, E. G. et al., *Hazardous Waste and Hazardous Materials* 6(1), 87–94, 1989.

Crain, N. et al. , *Ind. Eng. Chem. Res.* 32(10): 2259–68, 1993.

Crain, N. Supercritical Water Oxidation and Hydrolysis Kinetics of Pyridine and 2,4-Dichlorophenol. Master's Thesis, Civil Engineering Department, The University of Texas at Austin, 1993.

Gorchakov, L. N. et al., *Zashch. Met.* 25 (5) 656–658, 1990.

Holgate, H. R. et al., *Energy & Fuels* 6 (5):586–597, 1992.

Hudson, R. F., and L. Keay, *J. Chem. Soc.* pp. 2463–2469, 1956.

Huppert, G. L. et al., *Ind. Eng. Chem. Res.* 28:161–165, 1989.

Klein, M. T. et al., *J. Supercrit. Fluids* 3: 222–227, 1990

Lee, D. and E. F. Gloyna, "Supercritical Water Oxidation of Acetamide and Acetic Acid," Austin, Tex.: Center for Research in Water Resources, Technical Report CRWR-209, 1990.

McBrayer, R., Li, L., and Gloyna, E. F. Research and Development of a Commercial Supercritical Water Oxidation Process. *Proceedings of the Eleventh Annual Environmental Management and Technology Conference/International*, Atlantic City, N.J., Jun. 9–11, 1993.

Mill, T., and C. W. Gould, *Environ. Sci. Technol.* 13(2): 205–208, 1979.

Rollans, S. and E. F. Gloyna, "Behavior of Chromium During Supercritical Water Oxidation," Austin, Tex.: Center for Research in Water Resources, Technical Report CRWR-240, 1993.

Shanableh, A. M. Subcritical and Supercritical Water Oxidation of Industrial, Excess Activated Sludge. Ph.D. Dissertation, Civil Engineering Department, The University of Texas at Austin, Austin, Tex., 1990.

Tongdhamachart, C. Supercritical Water Oxidation of Anaerobically Digested Municipal Sludge. Ph.D. Dissertation, Civil Engineering Department, The University of Texas at Austin, Austin, Tex., 1991.

Torry, L. A. et al., The Effect of Salts on Hydrolysis in Supercritical Water: Reactivity and Availability, in The 2nd International Conference on Supercritical Fluids Held in Boston, Mass., M. A. McHugh, ed., 1991, pp. 425–428.

Townsend, S. H. et al., *Ind. Eng. Chem. Res.* 27:143–149, 1988

Townsend, S. H., and M. T. Klein, *Energy & Fuel*, 64:635, 1985.

Turner, M. D. Supercritical Water Oxidation of Dimethyl Methylphosphonate and Thiodiglycol. Ph.D. Dissertation, Civil Engineering Department, The University of Texas at Austin, Austin, Tex., 1993.

Weast, Robert C. and Melvin J. Astle, eds, CRC Handbook of Chemistry and Physics, 62d edition, Boca Raton, Fla., CRC Press, Inc., 1982.

Webley, P. A. et al., *Ind. Eng. Chem. Res.* 30(8): 1745–1754, 1991.

Webley, P. A. and J. W. Tester, "Fundamental Kinetics of Methanol Oxidation in Supercritical Water," in Supercritical Fluid Science and Technology, K. P. Johnston and J. M. L. Penninger, eds., ACS Symposium Series, American Chemical Society, Washington, 1989, pp. 259–275.

Webley, P. A., and J. W. Tester, *Energy & Fuels* 5(3):411–419, 1991.

Xu, X. et al., *J. Supercrit. Fluids* 3:228–232, 1990.

U.S. Pat. No. 3,984,311
U.S. Pat. No. 4,212,735
U.S. Pat. No. 4,483,761
U.S. Pat. No. 5,232,604
Japanese Patent JP 5031000
British Patent BR 8204075
German Patent 4215087
WO 9322490

It is understood that the examples and embodiments described herein are for illustrative purposes only and that various modifications in light thereof will be suggested to persons skilled in the art and are to be included within the spirit and purview of this application and scope of the appended claims.

What is claimed is:

1. A method of producing and recovering an alkane comprising:

mixing a reactant comprising an alkyl bound to a heteroatom, wherein the heteroatom is phosphorus, sulfur, nitrogen, arsenic, selenium or a halogen, with an additive that reacts with the heteroatom or with an oxidized heteroatom to form a salt insoluble in supercritical water; and reacting the mixture in supercritical water at an oxygen concentration favoring alkane production to form an alkane;

wherein formation of insoluble salt effects an equilibrium shift favoring alkane production; and recovering the alkane by separating it from other products of the reaction.

2. The method of claim 1 Wherein the oxygen concentration is at less than about 20% stoichiometric oxygen.

3. The method of claim 1 wherein the oxygen concentration is at less than about 1% stoichiometric oxygen.

4. The method of claim 1 wherein the alkane is methane, ethane propane or butane or isomers of butane.

5. The method of claim 1 wherein the alkane is methane.

6. A method of producing and recovering methane comprising:

mixing a reactant comprising an alkyl bound to a heteroatom, wherein the heteroatom is phosphorus, sulfur, nitrogen, arsenic, selenium or a halogen, with an additive that reacts with the heteroatom or an oxidized heteroatom to form a salt insoluble in supercritical water; and reacting the mixture in supercritical water at an oxygen concentration of less than about 20% stoichiometric to form methane;

wherein formation of insoluble salt effects an equilibrium shrill favoring methane production; and recovering the methane by separating it from other products of the reaction.

7. The method of claim 1 or 6 wherein the heteroatom is phosphorus, sulfur or nitrogen.

8. The method of claim 1 or 6 wherein the oxidized form of the heteroatom is phosphate, sulfate or nitrate.

9. The method of claim 1 or 6 wherein the heteroatom is halogen.

10. The method of claim 1 or 6 wherein the reactant comprises dialkyl alkylphosphonate or alkylphosphonic acid.

11. The method of claim 1 or 6 wherein the additive is a metal hydroxide, carbonate, borate or oxide.

12. The method of claim 11 wherein the metal is an alkali, an alkaline earth or a transition metal.

13. The method of claim 1 or 6 wherein the additive is NaOH, $Na_2CO_3$ or $Na_2B_4O_7$.

14. The method of claim 1 or 6 wherein the additive is NaOH.

15. A method of producing and recovering methane comprising:

mixing a reactant comprising an methyl bound to a heteroatom, wherein the heteroatom is phosphorus, sulfur, nitrogen, arsenic, selenium fluorine, chlorine, bromine or iodine, with a metal hydroxide, carbonate or borate to form a salt insoluble in supercritical water; and reacting the mixture in supercritical water at an oxygen concentration of less than about 20% stoichiometric to form methane;

wherein formation of insoluble salt effects an equilibrium shift favoring methane production; and recovering the methane by separating it from other products of the reaction.

16. The method of claim 15 wherein the metal is an alkali, an alkaline earth or a transition metal.

17. The method of claim 15 wherein the heteroatom is phosphorus, sulfur or nitrogen.

18. The method of claim 1 or 6 wherein the reactant is a component of wastewater.

19. The method of claim 1 or 6 wherein the reactant is a component of sludge.

20. A method of producing and recovering an alkane comprising:

mixing a reactant comprising an alkyl bound to a heteroatom, wherein the heteroatom is phosphorus, sulfur, nitrogen, arsenic, selenium, fluorine, chlorine, bromine or iodine, with an additive that reacts with the heteroatom or with an oxidized form of the heteroatom to form a salt insoluble in supercritical water; and reacting the mixture in water at a temperature from about 350° C. to about 500° C., a pressure of greater than about 22.1 MPa and at an oxygen concentration favoring alkane production to form an alkane;

wherein formation of insoluble salt effects an equilibrium shift favoring alkane production; and recovering the alkane by separating it from other products of the reaction.

21. A method of producing and recovering methane, ethane or propane, comprising:

mixing a reactant comprising an alkyl bound to a heteroatom, wherein the heteroatom is phosphorus, sulfur, nitrogen, arsenic, selenium, fluorine, chlorine, bromine or iodine, with an additive that reacts with the heteroatom or with an oxidized heteroatom to form a salt insoluble in supercritical water; and reacting the mixture in supercritical water at an oxygen concentration favoring production of methane, ethane or propane to form methane, ethane or propane;

wherein formation of insoluble salt effects an equilibrium shift favoring production of methane, ethane or propane; and recovering the methane, ethane or propane by separating it from other products of the reaction.

22. A method of producing an alkane comprising:

mixing a reactant comprising an alkyl bound to a phosphorus, sulfur, nitrogen, arsenic, selenium or halogen heteroatom with an additive to form a mixture; and heating the mixture under supercritical water conditions and at an oxygen concentration of less than about 1% stoichiometric oxygen so as to hydrolyze the alkyl bound to the heteroatom to form an alkane and at least one by-product heteroatom or oxidized heteroatom; and wherein the additive reacts with the by-product heteroatom or oxidized heteroatom to form a salt insoluble in supercritical water; and wherein formation of the insoluble salt effects an equilibrium shift favoring alkane production.

23. A method of producing methane, comprising:

contacting a methyl bound to a heteroatom under supercritical water conditions in the absence of oxygen and in the presence of an additive such that the methyl bound to the heteroatom hydrolyzes to form methane and a residue heteroatom or an oxidized heteroatom; and wherein the additive and the residue heteroatom or the oxidized heteroatom form an insoluble salt in supercritical water which effects an equilibrium shift favoring methane production.

24. The method of claim 1, 6, 15, 20, 21, 22, or 23 wherein the heteroatom is phosphorus and a phosphorus derivative is present in the form of a phosphate salt or as a phosphorus-based acid in either the precipitate or supercritical water phase.

* * * * *

UNITED STATES PATENT AND TRADEMARK OFFICE
CERTIFICATE OF CORRECTION

PATENT NO. : 5,565,616
DATED : October 15, 1996
INVENTOR(S) : Li et al.

It is certified that error appears in the above-indentified patent and that said Letters Patent is hereby corrected as shown below:

In claim 2, column 18, line 23, delete "Wherein" and insert --wherein-- therefor.

In claim 6, column 18, line 42, delete "shrill" and insert --shift-- therefor.

Signed and Sealed this

Twenty-fourth Day of December, 1996

Attest:

BRUCE LEHMAN

*Attesting Officer*  *Commissioner of Patents and Trademarks*